United States Patent
Oh

(10) Patent No.: US 9,939,507 B2
(45) Date of Patent: Apr. 10, 2018

(54) METHOD OF PROVIDING GUIDE INFORMATION FOR PHOTOGRAPHING OBJECT, METHOD OF RECOMMENDING OBJECT, AND MEDICAL IMAGE CAPTURING APPARATUS

(71) Applicant: Samsung Electronics Co., Ltd., Gyeonggi-do (KR)

(72) Inventor: Keum-yong Oh, Gyeonggi-do (KR)

(73) Assignee: Samsung Electronics Co., Ltd., Yeongton-gu, Suwon-si, Gyeonggi-do (KR)

( * ) Notice: Subject to any disclaimer, the term of this patent is extended or adjusted under 35 U.S.C. 154(b) by 773 days.

(21) Appl. No.: 14/050,700

(22) Filed: Oct. 10, 2013

(65) Prior Publication Data

US 2014/0378819 A1     Dec. 25, 2014

(30) Foreign Application Priority Data

Jun. 21, 2013  (KR) ..................... 10-2013-0071946

(51) Int. Cl.
  *A61B 5/055*   (2006.01)
  *G01R 33/54*   (2006.01)
  *G01R 33/56*   (2006.01)

(52) U.S. Cl.
  CPC ............ *G01R 33/546* (2013.01); *A61B 5/055* (2013.01); *G01R 33/5601* (2013.01)

(58) Field of Classification Search
  CPC ... A61B 5/055; G01R 33/546; G01R 33/5601
  See application file for complete search history.

(56) References Cited

U.S. PATENT DOCUMENTS

| 8,744,156 B2 | 6/2014 | Abe |
| 8,805,476 B2 | 8/2014 | Yang |
| 2004/0128164 A1* | 7/2004 | DeJarnette ............ G06F 19/321 705/2 |
| 2004/0213444 A1 | 10/2004 | Yamamichi |
| 2009/0149737 A1 | 6/2009 | Hansen et al. |
| 2009/0216110 A1 | 8/2009 | Piron et al. |
| 2013/0053683 A1 | 2/2013 | Hwang et al. |

FOREIGN PATENT DOCUMENTS

| CN | 101803921 A | 8/2010 |
| JP | 2009-119281 A | 6/2009 |

OTHER PUBLICATIONS

ASPECT Magnet Technology Ltd. M2 User Guide Nov. 2010, pp. 1-105.*

* cited by examiner

*Primary Examiner* — Ruth S Smith
(74) *Attorney, Agent, or Firm* — Cha & Reiter, LLC

(57) ABSTRACT

A system provides guidance information for guiding sequencing and acquisition of medical images of objects by obtaining first imaging configuration information of a first object and second imaging configuration information of a second object. The system classifies the first imaging configuration information into, changing information indicating a difference between the first and second imaging configuration and unchanging information indicating no difference between the first and second imaging configuration, by comparing the first imaging configuration information and the second imaging configuration information. The system outputs the changing information as guide information for imaging the second object.

61 Claims, 20 Drawing Sheets

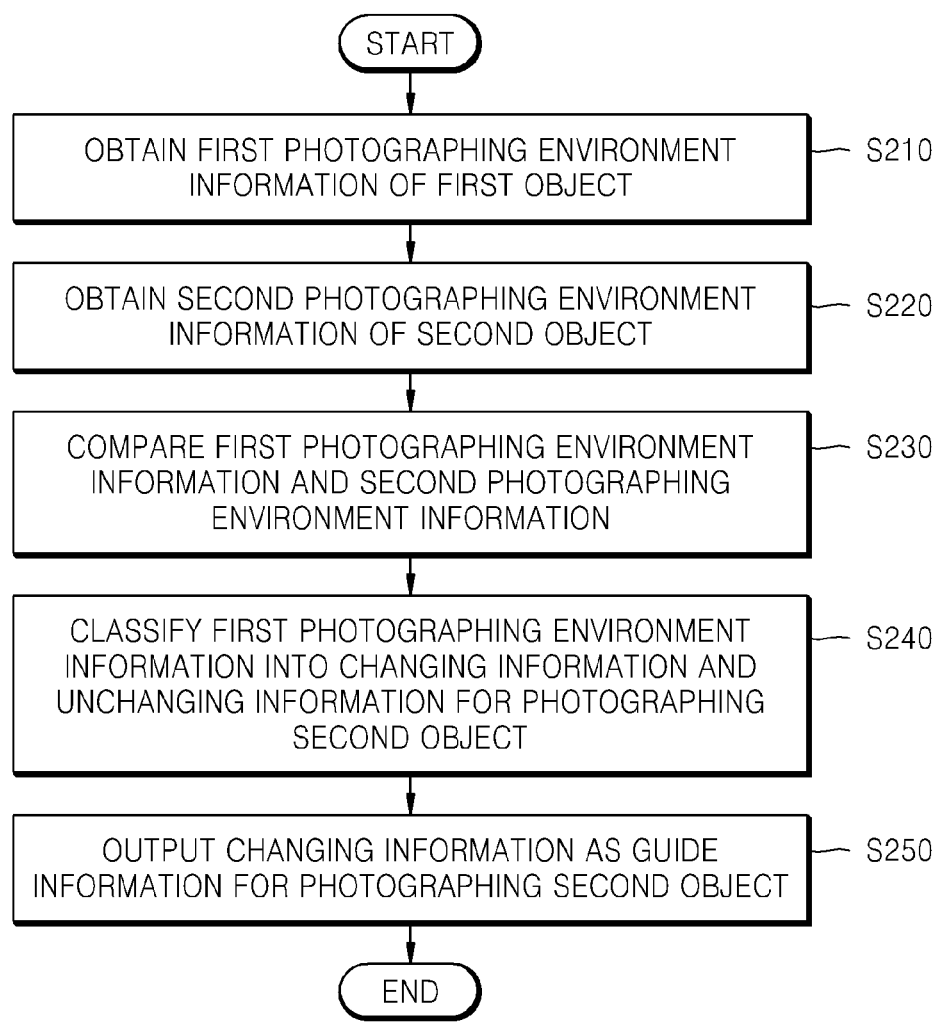

FIG. 3A

| FIRST PHOTOGRAPHING ENVIRONMENT INFORMATION | |
|---|---|
| ECG MEASURER | MOUNT |
| CONTRAST MEDIUM INJECTOR | MOUNT |
| RESPIRATION MEASURER | MOUNT |
| TEMPERATURE MEASURER | UNMOUNT |

FIG. 3B

| SECOND PHOTOGRAPHING ENVIRONMENT INFORMATION | |
|---|---|
| ECG MEASURER | UNMOUNT |
| CONTRAST MEDIUM INJECTOR | MOUNT |
| RESPIRATION MEASURER | UNMOUNT |
| TEMPERATURE MEASURER | UNMOUNT |

FIG. 3C

| GUIDE INFORMATION FOR PHOTOGRAPHING SECOND OBJECT | | |
|---|---|---|
| CHANGING INFORMATION (310) | ECG MEASURER | REMOVE |
| | RESPIRATION MEASURER | REMOVE |
| UNCHANGING INFORMATION (330) | CONTRAST MEDIUM INJECTOR | RETAIN |
| | TEMPERATURE MEASURER | RETAIN |

GUIDE INFORMATION (510)

| FIRST RF COIL (512) | |
|---|---|
| HEAD RF COIL | RETAIN |
| NECK RF COIL | RETAIN |

| SECOND RF COIL (514) | |
|---|---|
| LEG RF COIL | REMOVE |
| | |
| | |
| | |

OBJECT INFORMATION (520)

TEST INFORMATION (530)

OBJECT LIST (540)

| Index | Name | ID | Gender | Study Name | Date / Time |
|---|---|---|---|---|---|
| 1 | A | MRN0000001 | M | Sella MRI | 02/20/2011 10.10 |
| 2 | B | MRN0000002 | M | Branin MRI | 02/20/2011 10.10 |
| 3 | C | MRN0000003 | F | Internal Audt. | 02/20/2011 10.10 |
| 4 | D | MRN0000004 | F | Sella MRI | 02/20/2011 10.10 |
| ... | ... | ... | ... | ... | ... |

| NAME | PHOTOGRAPHING ENVIRONMENT INFORMATION | |
|---|---|---|
| A | HEAD RF COIL | MOUNT |
|   | LEG RF COIL | MOUNT |

FIG. 12B

| NAME | PHOTOGRAPHING ENVIRONMENT INFORMATION | |
|---|---|---|
| B | NECK RF COIL | MOUNT |

| NAME | PHOTOGRAPHING ENVIRONMENT INFORMATION | |
|---|---|---|
| C | HEAD RF COIL | MOUNT |
|   | LEG RF COIL | MOUNT |

| NAME | PHOTOGRAPHING ENVIRONMENT INFORMATION | |
|---|---|---|
| D | LEG RF COIL | MOUNT |

FIG. 13A

| NAME | PHOTOGRAPHING ENVIRONMENT INFORMATION | |
|---|---|---|
| A | HEAD RF COIL | MOUNT |
| | LEG RF COIL | MOUNT |

FIG. 13B

| NAME | PHOTOGRAPHING ENVIRONMENT INFORMATION | |
|---|---|---|
| B | NECK RF COIL | MOUNT |

| NAME | PHOTOGRAPHING ENVIRONMENT INFORMATION | |
|---|---|---|
| C | HEAD RF COIL | MOUNT |
| | LEG RF COIL | MOUNT |
| | NECK RF COIL | MOUNT |
| | ABDOMEN RF COIL | MOUNT |

| NAME | PHOTOGRAPHING ENVIRONMENT INFORMATION | |
|---|---|---|
| D | HEAD RF COIL | MOUNT |
| | LEG RF COIL | MOUNT |
| | ABDOMEN RF COIL | MOUNT |

FIG. 14A

| NAME | PHOTOGRAPHING ENVIRONMENT INFORMATION ||
|---|---|---|
| A | HEAD RF COIL | MOUNT |
|   | LEG RF COIL | MOUNT |

FIG. 14B

| NAME | PHOTOGRAPHING ENVIRONMENT INFORMATION ||
|---|---|---|
| B | NECK RF COIL | MOUNT |

| NAME | PHOTOGRAPHING ENVIRONMENT INFORMATION ||
|---|---|---|
| C | HEAD RF COIL | MOUNT |
|   | LEG RF COIL | MOUNT |
|   | NECK RF COIL | MOUNT |

| NAME | PHOTOGRAPHING ENVIRONMENT INFORMATION ||
|---|---|---|
| D | HEAD RF COIL | MOUNT |
|   | LEG RF COIL | MOUNT |
|   | ABDOMEN RF COIL | MOUNT |

FIG. 15A

| NAME | PHOTOGRAPHING ENVIRONMENT INFORMATION ||
|---|---|---|
| A | HEAD RF COIL | MOUNT |
|   | ABDOMEN RF COIL | MOUNT |
|   | NECK RF COIL | MOUNT |
|   | LEG RF COIL | MOUNT |

FIG. 15B

| NAME | PHOTOGRAPHING ENVIRONMENT INFORMATION ||
|---|---|---|
| B | NECK RF COIL | MOUNT |

| NAME | PHOTOGRAPHING ENVIRONMENT INFORMATION ||
|---|---|---|
| C | HEAD RF COIL | MOUNT |
|   | ABDOMEN RF COIL | MOUNT |

| NAME | PHOTOGRAPHING ENVIRONMENT INFORMATION ||
|---|---|---|
| D | HEAD RF COIL | MOUNT |
|   | ABDOMEN RF COIL | MOUNT |
|   | LEG RF COIL | MOUNT |

FIG. 16A

| NAME | PHOTOGRAPHING ENVIRONMENT INFORMATION ||
|---|---|---|
| A | HEAD RF COIL | MOUNT |
| | ABDOMEN RF COIL | MOUNT |
| | NECK RF COIL | MOUNT |
| | LEG RF COIL | MOUNT |

FIG. 16B

| NAME | PHOTOGRAPHING ENVIRONMENT INFORMATION ||
|---|---|---|
| B | NECK RF COIL | MOUNT |

| NAME | PHOTOGRAPHING ENVIRONMENT INFORMATION ||
|---|---|---|
| C | HEAD RF COIL | MOUNT |
| | ABDOMEN RF COIL | MOUNT |
| | NECK RF COIL | MOUNT |

| NAME | PHOTOGRAPHING ENVIRONMENT INFORMATION ||
|---|---|---|
| D | HEAD RF COIL | MOUNT |
| | ABDOMEN RF COIL | MOUNT |
| | LEG RF COIL | MOUNT |

METHOD OF PROVIDING GUIDE INFORMATION FOR PHOTOGRAPHING OBJECT, METHOD OF RECOMMENDING OBJECT, AND MEDICAL IMAGE CAPTURING APPARATUS

CROSS-REFERENCE TO RELATED PATENT APPLICATION

This application claims the benefit of Korean Patent Application No. 10-2013-0071946, filed on Jun. 21, 2013, in the Korean Intellectual Property Office, the disclosure of which is incorporated herein in its entirety by reference.

BACKGROUND

1. Field of the Invention

A system concerns providing guide information about an object for which a medical image is to be captured, recommending an object based on imaging environment information and associated medical image acquisition.

2. Description of the Related Art

A user of a medical image acquisition system acquires images of many patients per day, and needs to change imaging environment in response to, to patient medical condition (e.g., disease) and patient anatomical region concerned. However, it is burdensome to a user to change image acquisition parameters and environment for each patient.

In a magnetic resonance imaging (MRI) system, a type of a radio frequency (RF) coil to be mounted on a patient differs with patient. A user needs to select and mount an RF coil to acquire an MRI image based on image acquisition environment of each patient and to remove an unnecessary RF coil from the MRI apparatus when a patient is to be imaged.

SUMMARY

The inventors have advantageously recognized a need for a user friendly system for easily changing a medical imaging environment, equipment and settings of a medical imaging system.

A system provides guide information, recommends an object, and a medical image capturing apparatus, facilitating user change of an imaging system environment.

A system provides guidance information for guiding sequencing and acquisition of medical images of objects by obtaining first imaging configuration information of a first object and second imaging configuration information of a second object. The system classifies the first imaging configuration information into, changing information indicating a difference between the first and second imaging configuration and unchanging information indicating no difference between the first and second imaging configuration, by comparing the first imaging configuration information and the second imaging configuration information. The system outputs the changing information as guide information for imaging the second object.

In a feature, the outputting comprises outputting information identifying how the changing information is to be changed to image the second object and the second object comprises an object to be imaged after the first object is imaged. The imaging configuration information comprises information identifying at least one of, a type of a radio frequency (RF) coil to be mounted on an object, a contrast medium injector is to be used for an object, an electrocardiogram (ECG) device is to be used for an object, a respiration device is to be used for an object, and a temperature measurement device is to be used for an object. The classifying comprises classifying at least one RF coil to be mounted on the first object into a first RF coil to be mounted also on the second object and a second RF coil not to be mounted on the second object, and the outputting comprises distinguishing and outputting information identifying the first RF coil and information identifying the second RF coil. The classifying also comprises classifying the at least one RF coil into the first RF coil and the second RF coil in response to at least one of, mounting anatomical region, channel number, clinical purpose, and size of RF coil. The outputting also comprises outputting information identifying a third RF coil that is not to be mounted on the first object but to be mounted on the second object by distinguishing the information identifying the third RF coil from the information identifying the first and second RF coils. Further, the outputting comprises displaying the information identifying the first RF coil and the information identifying the second RF coil on a display.

In another feature, the displaying comprises displaying an RF coil model corresponding to the at least one RF coil to be mounted on the first object at a location of an object model displayed on the display, the location corresponding to a mounting region of the at least one RF coil to be mounted on the first object. The displaying also comprises displaying a first RF coil model in a first color, and displaying a second RF coil model in a second color.

Also the displaying comprises displaying a third RF coil model corresponding to a third RF coil that is not to be mounted on the first object but to be mounted on the second object in a third color at a location corresponding to a mounting region of the third RF coil on the object model. Further, the third RF coil model is displayed in the third color, wherein at least one of brightness, chroma, and hue of the third color is changed in response to at least one of an anatomical mounting region, a clinical purpose, a channel number, and a size of the third RF coil.

In another feature, a method provides guidance information for guiding sequencing and acquisition of medical images of objects using a medical imaging system, by obtaining information identifying at least one radio frequency (RF) coil to be mounted on an object and information identifying at least one RF coil mounted on a medical image acquisition apparatus. The method classifies the at least one RF coil mounted on the medical image acquiring apparatus into a first RF coil to be mounted also on the object and a second RF coil that is not to be mounted on the object, by comparing the information identifying the at least one RF coil to be mounted on the object and the information identifying the at least one RF coil mounted on the medical image acquiring apparatus. Guidance information is output identifying the first RF coil, and information identifying the second RF coil and distinguishing the first and second RF coils for use in imaging the object.

In another feature, the outputting comprises outputting information identifying a third RF coil that is not mounted on the medical image acquiring apparatus but is to be mounted on the object, by distinguishing the information identifying the third RF coil from the information identifying the first and second RF coils. The outputting comprises transmitting identification information of the third RF coil to a plurality of RF coils that are not mounted on the medical image acquisition apparatus and comprises displaying the information identifying the first RF coil and the information identifying the second RF coil on a display. Further, the displaying comprises displaying the information identifying the first RF coil and the information identifying the second RF coil on a display attached to a gantry surface of the medical image acquisition apparatus. Additionally, the displaying comprises displaying an RF coil model corresponding to the at least one RF coil mounted on the medical image acquisition apparatus at a location corresponding to a mounting region of the at least one RF coil mounted on the medical image acquisition apparatus, from among an object model displayed on the display. Also the displaying comprises displaying a first RF coil model corresponding to the first RF coil in a first color and a second RF coil model corresponding to the second RF coil in a second color, on an RF coil model displayed on the object model. The displaying also comprises displaying a third RF coil model corresponding to a third RF coil that is not mounted on the medical image acquisition apparatus but is to be mounted on the object, in a third color at a location corresponding to a mounting region of the third RF coil on the object model.

In yet another feature, the displaying comprises, when the third RF coil is mounted on the medical image acquisition apparatus, displaying the third RF coil model displayed on the object model in the first color changed from the third color. Also, when an RF coil mounted on the medical image acquisition apparatus is removed, the method does not display an RF coil model corresponding to the RF coil removed from the medical image acquisition apparatus on the object model.

In another feature, a method selects an object for to be imaged using a medical imaging system by obtaining first imaging configuration information identifying a first object and obtaining second imaging configuration information identifying each of a plurality of second objects. The method selects a third object to be imaged after the first object is imaged, from among the plurality of second objects, by comparing the first imaging configuration information and the second imaging configuration information identifying each of the plurality of second objects. Information identifying the selected third object is output. The selecting of the third object comprises selecting an object to be imaged using the same number and type of RF coils as used in imaging the first object. The method determines a second plurality of second objects on which an RF coil used in imaging the first object is to be mounted and at least one RF coil that is not used in imaging the first object is to be additionally mounted and selects the third object from among the determined second plurality of second objects based on the number of RF coils to be additionally mounted on the second plurality of second objects.

In yet another feature, the third object from among the determined second plurality of second objects comprises selecting an object on which the least number RF coils are to be additionally mounted. The method selects the third object by obtaining information identifying the number of RF coils to be removed from a first object imaging configuration for imaging each of the plurality of second objects; and selecting the third object from among the plurality of second objects based on the obtained information identifying the number of RF coils. The selection of the third object from among the plurality of second objects comprises selecting an object having the least number of RF coils to be removed as the third object, from among the plurality of second objects.

In an additional feature the selecting of the third object comprises: determining the similarity between at least one RF coil to be mounted on the first object and at least one RF coil to be mounted on each of the plurality of second objects; and selecting a second object having the highest similarity from among the plurality of second objects, as the third object. The determining of the similarity comprises: setting a similarity value according to mounting regions of each RF coil; and determining the similarity between the at least one RF coil to be mounted on the first object and the at least one RF coil to be mounted on each of the plurality of second objects based on the set similarity value. The selecting of the third object comprises, when an imaging order of the plurality of second objects is predetermined, selecting the third object from second objects in response to the predetermined order. The outputting comprises outputting changing information for imaging the third object from among the first imaging configuration information, as guide information for imaging the third object.

BRIEF DESCRIPTION OF THE DRAWINGS

The above and other features and advantages of the present invention will become more apparent by describing in detail exemplary embodiments thereof with reference to the attached drawings in which:

FIG. 2 shows a flowchart illustrating a method of providing guide information, according to invention principles;

FIG. 3A shows a table of first photographing environment information of a first object, FIG. 3B shows a table of second photographing environment information of a second object, and FIG. 3C shows a table of guide information for photographing the second object, according to invention principles;

FIG. 5 shows guide information output from a display of the medical image capturing apparatus, according to invention principles;

FIGS. 12A and 12B show tables used by a method of determining a third object from among a plurality of second objects, according to invention principles;

FIGS. 13A and 13B show tables used by a method of determining a third object from among a plurality of second objects, according to invention principles;

FIGS. 14A and 14B show tables used by a method of determining a third object from among a plurality of second objects, according to invention principles;

FIGS. 15A and 15B show tables used by a method of determining a third object from among a plurality of second objects, according to invention principles;

FIGS. 16A and 16B show tables used by a method of determining a third object from among a plurality of second objects, according to invention principles;

DETAILED DESCRIPTION

Figure 1:
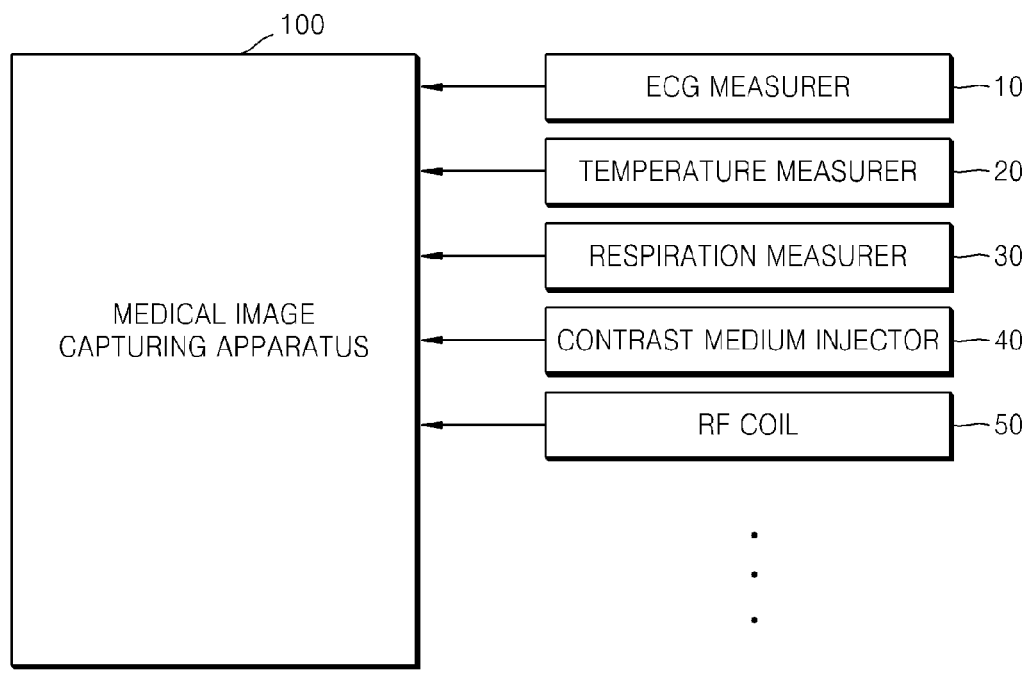
FIG. 1 shows a medical image capturing apparatus and peripheral devices mountable on the medical image capturing apparatus, according to invention principles.

One or more embodiments of the present invention will now be described more fully with reference to the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Terms widely used are selected while considering functions in one or more embodiments of the present invention for terms used herein, but the terms used herein may differ according to intentions of one of ordinary skill in the art, precedents, or emergence of new technologies. Also, in some cases, an applicant arbitrarily selects a term, and in this case, the meaning of the term will be described in detail herein. Accordingly, the terms shall be defined based on the meanings and details throughout the specification, rather than the simple names of the terms. The term "environment" concerning an imaging environment is used interchangeably herein with the term "configuration". Further, "imaging configuration information" comprises information indicating imaging settings, and peripheral devices such as ECG, temperature, respiration, contrast injection and RF coil devices, used in an imaging setup for imaging a portion of patient anatomy (an object), for example.

When something "includes" a component, another component may be further included unless specified otherwise. The term "unit" used in the present specification refers to a software component, or a hardware component such as FPGA or ASIC, and performs a certain function. However, the "unit" is not limited to software or hardware. The "unit" may be configured in an addressable storage medium and may be configured to be executed by one or more processors. Hence, the "unit" includes elements such as software elements, object-oriented software elements, class elements, and task elements, and processes, functions, attributes, procedures, sub-routines, segments of program codes, drivers, firmware, micro-codes, circuits, data, databases, data structures, tables, arrays, and variables. The functions provided in the elements and the units may be combined into a fewer number of elements and units or may be divided into a larger number of elements and units.

While describing one or more embodiments of the present invention, descriptions about drawings that are not related to the one or more embodiments of the present invention are omitted.

As used herein, the term "and/or" includes any and all combinations of one or more of the associated listed items. Expressions such as "at least one of," when preceding a list of elements, modify the entire list of elements and do not modify the individual elements of the list.

In the present specification, "image" may refer to multi-dimensional data composed of discrete image elements (e.g., pixels in a two-dimensional image and voxels in a three-dimensional image). For example, an image may include a medical image of an object acquired by an X-ray, computed tomography (CT), magnetic resonance imaging (MRI), ultrasonic waves, or another medical image photographing apparatus.

Furthermore, in the present specification, "object" may include a person or an animal, or a part of a person or an animal. For example, the object may include the liver, the heart, the womb, the brain, a breast, the abdomen, or a blood vessel. Furthermore, the "object" may include a phantom. The phantom means a material having a volume that is approximately the intensity and effective atomic number of a living thing, and may include a sphere phantom having a property similar to a human body.

Furthermore, in the present specification, "user" refers to a medical professional, such as a doctor, a nurse, a medical laboratory technologist, and an engineer who repairs a medical apparatus, but the user is not limited thereto.

Furthermore, in the present specification, "MRI" refers to an image of an object obtained by using the nuclear magnetic resonance principle.

Furthermore, in the present specification, "pulse sequence" refers to continuity of signals repeatedly applied by an MRI apparatus. A pulse sequence may include a time parameter of a radio frequency (RF) pulse, for example, repetition time (TR) or echo time (TE).

Furthermore, in the present specification, "pulse sequence mimetic diagram" shows an order of events that occur in an MRI apparatus. For example, a pulse sequence mimetic diagram may be a diagram showing an RF pulse, a gradient magnetic field, or an MR signal according to time.

FIG. 1 shows medical image capturing apparatus 100 and associated peripheral devices. Apparatus 100 may include an MRI apparatus, a CT apparatus, an X-ray apparatus, or a positron emission tomography (PET) apparatus. The plurality of peripheral devices may be mounted on the medical image capturing apparatus 100 of FIG. 1. Peripheral devices include an electrocardiogram (ECG) measurer 10 for measuring ECG of an object, a temperature measurer 20 for measuring a temperature of an object, a respiration measurer 30 for measuring the respiration of an object, a contrast medium injector 40 for injecting a contrast medium to an object, and an RF coil 50 for emitting or receiving an RF signal to or from an MRI apparatus. Other various peripheral devices that are well known to one of ordinary skill in the art may also be mounted on the medical image capturing apparatus 100, as well as those shown in FIG. 1. The plurality of peripheral devices may be separated from the medical image capturing apparatus 100 according to a photographing environment of an object. Apparatus 100 provides intuitive information about which peripheral device is to be mounted on the medical image capturing apparatus 100 for imaging an object and specific patient.

FIG. 2 shows a flowchart of a method of providing guide information. In operation S210, the medical image capturing apparatus 100 obtains first imaging environment (configuration) information of a first object and in operation S220, apparatus 100 obtains second photographing environment information of a second object. Photographing environment information of an object includes information about which peripheral devices are to be mounted on the medical image capturing apparatus 100 to photograph the object. In detail, the photographing environment information include information about at least one of, a type of RF coil 50 to be mounted on the medical image capturing apparatus 100, whether the contrast medium injector 40 is to be used for the object, whether the ECG measurer 10 is to be used for the object, whether the respiration measurer 30 is to be used for the object, and whether the temperature measurer 20 is to be used for the object. If the medical image capturing apparatus 100 is not an MRI apparatus, the photographing environment information does not include information about the type of the RF coil 50.

The medical image capturing apparatus 100 determines the first and second photographing environment information based on information about diseases, photographed regions, or photographing modes of the first and second objects, or receives the first and second photographing environment information from an external server. In operation S230, the medical image capturing apparatus 100 compares the first photographing environment information and the second photographing environment information. In operation S240, the medical image capturing apparatus 100 classifies the first photographing environment information into changing information and unchanging information for photographing the second object. For example, when the first photographing environment information indicates that the contrast medium injector 40 and the ECG measurer 10 are to be used, and the second photographing environment information indicates that the ECG measurer 10 is to be used, information that the contrast medium injector 40 is to be used is determined to be changing information and information that the ECG measurer 10 is to be used is determined to be unchanging information, from the first photographing environment information.

In operation S250, the medical image capturing apparatus 100 outputs the changing information in the first photographing environment information as guide information for photographing the second object. The user determines how to change a photographing environment of the first object in order to photograph the second object, through the guide information output by the medical image capturing apparatus 100.

FIG. 3A shows a table of the first photographing environment information of the first object, FIG. 3B shows a table of the second photographing environment information of the second object, and FIG. 3C shows a table of the guide information for photographing the second object. The first photographing environment information shown in FIG. 3A indicates that the ECG measurer 10, the contrast medium injector 40, and the respiration measurer 30 are to be mounted and the temperature measure 20 is not to be mounted in order to capture a medical image of the first object. Also, the second photographing environment information shown in FIG. 3B indicates that only the contrast medium injector 40 is to be mounted and the ECG measurer 10, the respiration measurer 30, and the temperature measurer 20 are not to be mounted in order to capture a medical image of the second object.

The medical image capturing apparatus 100 compares the first photographing environment information and the second photographing environment information, and determines information about the ECG measurer 10 and the respiration measurer 30 as changing information 310 for photographing the second object, and information about the contrast medium injector 40 and the temperature measurer 20 as unchanging information 330, from the first photographing environment information. Referring to FIG. 3C, the medical image capturing apparatus 100 outputs the information about the ECG measurer 10 and the respiration measurer 30, which is the changing information 310 in the first photographing environment information. Also, the medical image capturing apparatus 100 outputs information about how to change the changing information 310 together with the changing information 310, in order to photograph the second object. FIG. 3C shows that the ECG measurer 10 and the respiration measurer 30 are to be removed in order to photograph the second object.

Alternatively, the medical image capturing apparatus 100 classifies and outputs the changing information 310 and the unchanging information 330 in the first photographing environment information, as shown in FIG. 3C. Accordingly, the user easily determines from the guide that the ECG measurer 10 and the respiration measurer 30 are to be removed and the contrast medium injector 40 and temperature measurer 20 are not to be removed from apparatus 100.

If the second photographing environment information shown in FIG. 3B indicates that a peripheral device that is not to be mounted for the first object is to be mounted on the medical image capturing apparatus 100, the medical image capturing apparatus 100 distinguishes and output information about the corresponding peripheral device from the changing information 310 and the unchanging information 330. Accordingly, the user easily determine that the peripheral device is to be additionally mounted on the medical image capturing apparatus 100 in order to photograph the second object after photographing the first object.

Figure 4:
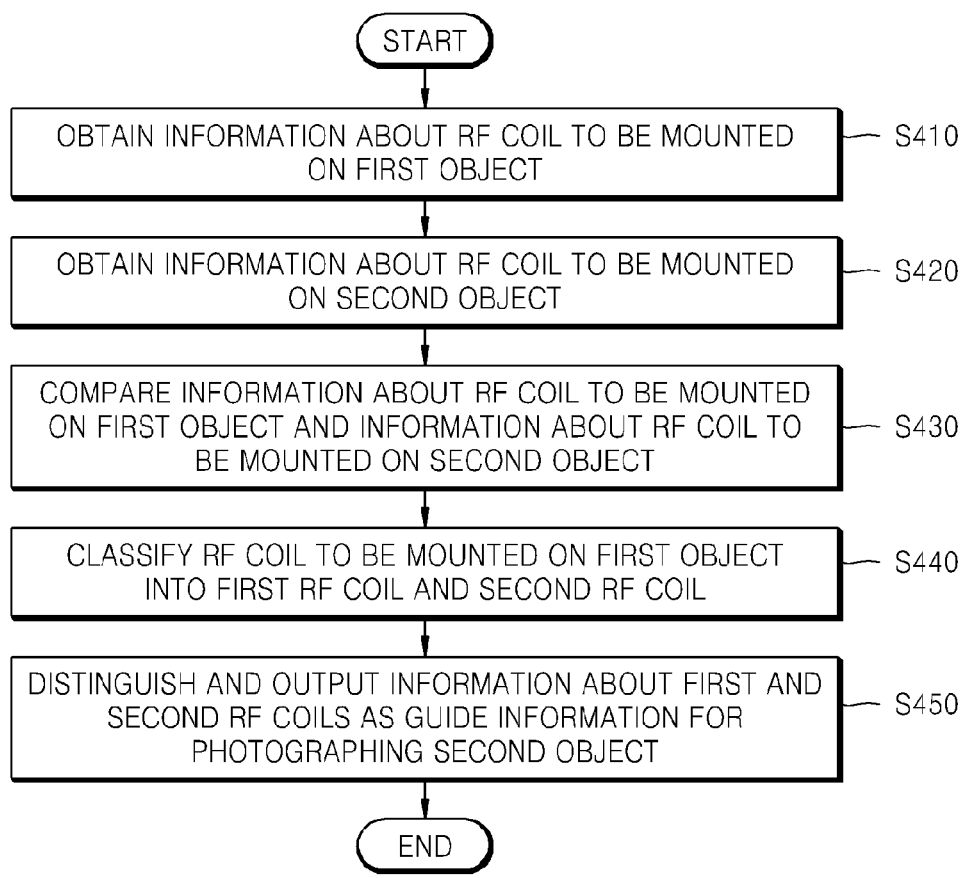
FIG. 4 shows a flowchart illustrating a method of providing guide information, according to invention principles.

FIG. 4 shows a flowchart of a method of providing guide information. An MRI medical image capturing apparatus 100 in operation S410 acquires information about at least one RF coil 50 to be mounted on the first object. In operation S420, the medical image capturing apparatus 100 obtains information about at least one RF coil 50 to be mounted on the second object. The medical image capturing apparatus 100 obtains the information based on the data identifying the medical condition (disease), anatomical region to be imaged, and the imaging modes of the first and second objects. Information about an RF coil includes information about which type of RF coil is required to image an object. In operation S430, the medical image capturing apparatus 100 compares the information about at least one RF coil to be mounted on the first object and the information about at least one RF coil to be mounted on the second object. In operation S440, the medical image capturing apparatus 100 classifies the at least one RF coil to be mounted on the first object into a first RF coil type to be mounted also on the second object and a second RF coil type not to be mounted on the second object.

The apparatus 100 determines the head RF coil as the first RF coil, and the leg RF coil as the second RF coil. Apparatus 100 also determines the at least one RF coil to be mounted on the first object includes a head RF coil and a leg RF coil, and the at least one RF coil to be mounted on the second object includes the head RF coil, The apparatus 100 classifies the at least one RF coil to be mounted on the first object as a first or second RF coil in response to, mounting regions, channel numbers, purposes, and sizes of the at least one RF coil to be used for imaging the first and second objects. Accordingly, if a head RF coil is to be mounted on the first object and second object but with different channel numbers, apparatus 100 treats the head RF coils as being different (e.g. as first and second RF coils).

In operation S450, the medical image capturing apparatus 100 derives and outputs information about the first and second RF coils. A user readily determines from the guide information an RF coil to be mounted on apparatus 100 and an RF coil to be removed from apparatus 100 in order to image a particular object (e.g. second object).

FIG. 5 shows guide information 510 output via a display 500 of the medical image capturing apparatus 100.

The apparatus 100 outputs an object list 540 of objects to be imaged. The object list 540 includes identification (ID) information including names and IDs of the objects, or study names. An index number indicates imaging order. Hereinafter, an object corresponding to an index no. 1 is referred to as a first object 550, and an object corresponding to an index no. 2 is referred to as a second object 570. When the user selects the second object 570, the apparatus 100 outputs the guide information 510 for imaging the second object 570. Also, as shown in FIG. 5, the apparatus 100 further outputs object information 520 and test information 530 of the second object 570. However, the object information 520 and the test information 530 may be omitted.

The apparatus 100 compares information about at least one RF coil to be mounted on the first object 550 and information about at least one RF coil to be mounted on the second object 570, and classifies the at least one RF coil to be mounted on the first object 550 into a first RF coil 512 to be also mounted on the second object 570 and a second RF coil 514 not to be mounted on the second object 570. The apparatus 100 distinguishes and outputs the first RF coil 512 and the second RF coil 514 guide information 510 for imaging the second object 570. Head and neck RF coils are the first RF coil 512, and a leg RF coil is the second RF coil 514. In response to imaging first object 550, the user keeps the head and neck RF coils mounted on the apparatus 100, and removes the leg RF coil to image the second object 570.

Apparatus 100 outputs guide information 510 identifying difference between imaging environment information of the second object 570 selected by the user and imaging environment information of the first object 550 imaged before the second object 570. Thereby a user intuitively determines the imaging environment information of the second object 570 without having to compare the imaging environment information of the first object 550 and the imaging environment information of the second object 570.

Figure 6:
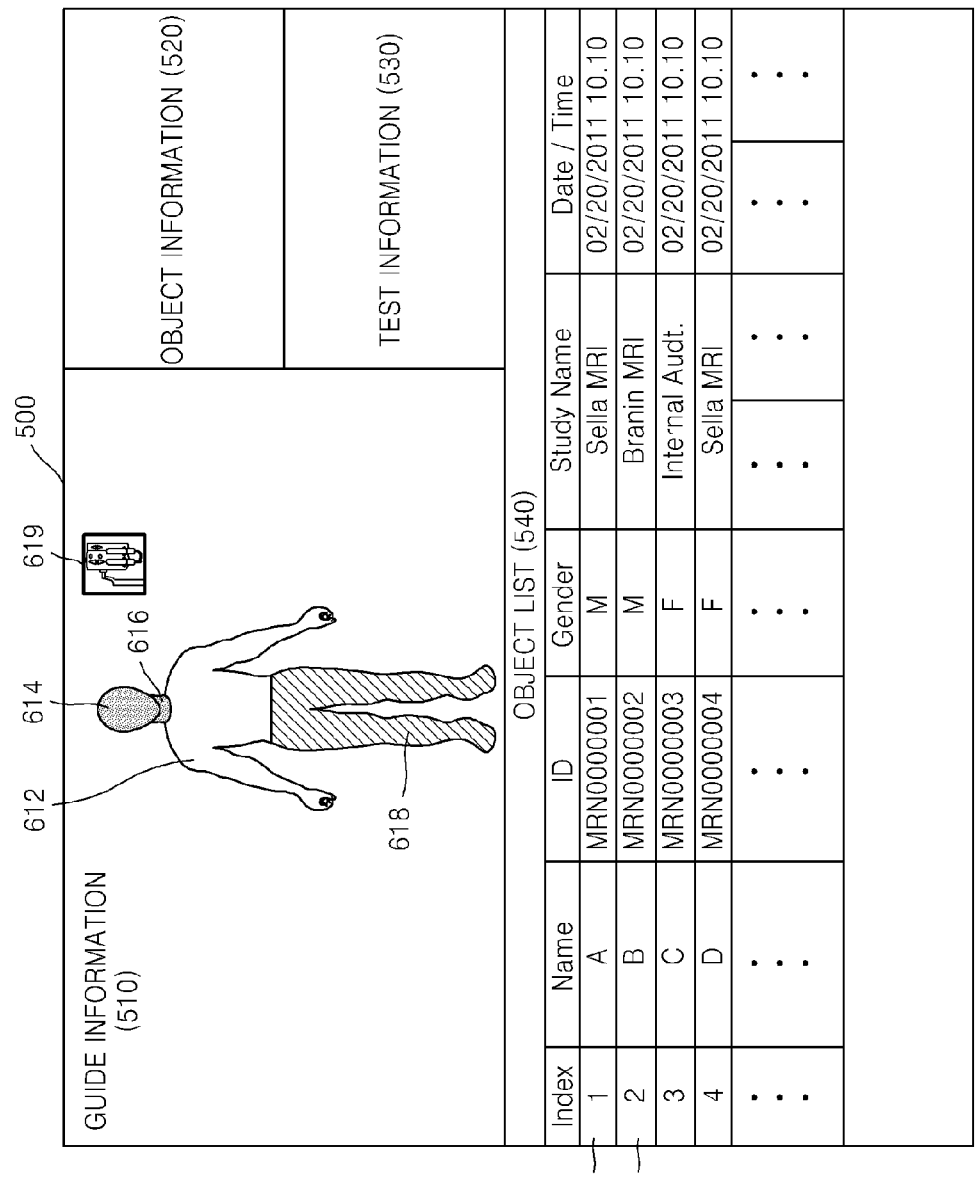
FIG. 6 shows guide information output from the display of the medical image capturing apparatus, according to invention principles.

FIG. 6 shows guide information 510 output from the display 500 of the apparatus 100. Apparatus 100 displays guide information 510 for imaging the second object 570 selected by the user, as an object model 612 and RF coil models corresponding to the at least one RF coil to be mounted on the first object 550. Apparatus 100 displays the RF coil models at locations corresponding to mounting regions of the at least one RF coil to be mounted on the first object 550 on the object model 612. Here, the apparatus 100 distinguishes and displays the RF coil models as first RF coil models 614 and 616 corresponding to a first RF coil and a second RF coil model 618 corresponding to a second RF coil, on the object model 612. For example, the apparatus 100 displays the first RF coil models 614 and 616 in a first color and the second RF coil model 618 in a second color for distinction. The user determines that the first RF coil models 614 and 616 displayed in the first color are RF coils to be kept on the apparatus 100 after the first object 550 is imaged, and that the second RF coil model 618 displayed on the second color is an RF coil to be removed from the apparatus 100 after the first object 550 is imaged. Apparatus 100 displays the first RF coil models 614 and 616 respectively corresponding to head and neck RF coils in the first color and the second RF coil model 618 corresponding to a leg RF coil in the second color so that the user determines that the leg RF coil displayed on the second color is to be removed in order to image the second object 570.

Also, the guide information 510 of FIG. 6 includes a contrast medium injector model 619 corresponding to a contrast medium injector. The contrast medium injector model 619 indicates information about whether the contrast medium injector is to be mounted on or removed from the apparatus 100 in order to image the second object 570. For example, when the contrast medium injector is to be mounted on the apparatus 100 in order to image the second object 570, the apparatus 100 display the contrast medium injector model 619 in the first color; however, when the contrast medium injector is to be removed from the apparatus 100 in order to image the second object 570, the apparatus 100 displays the contrast medium injector model 619 in the second color.

Figure 7:
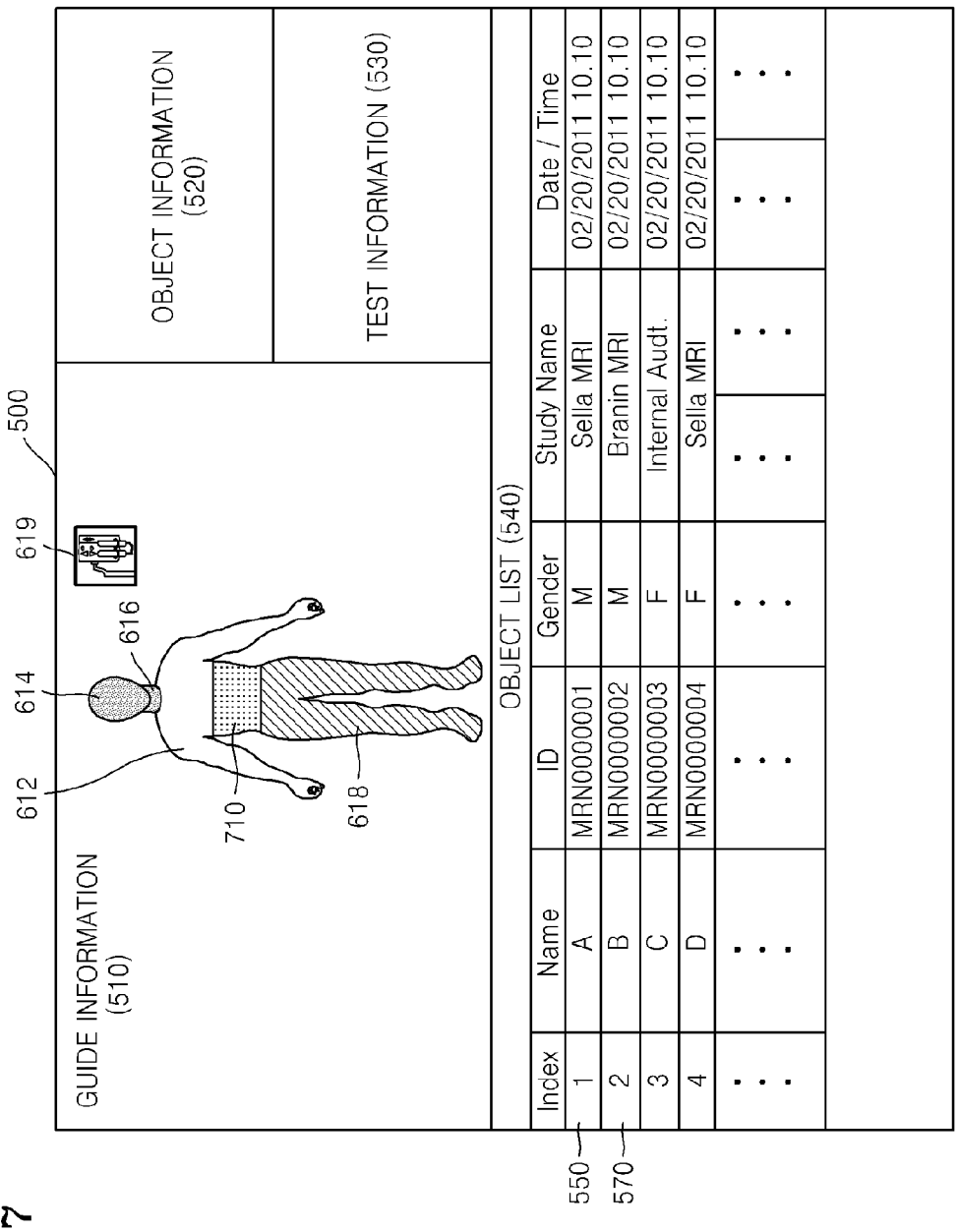
FIG. 7 shows guide information output from the display of the medical image capturing apparatus, according to invention principles.

FIG. 7 shows guide information 510 output from the display 500 of the apparatus 100. The at least one RF coil to be mounted on the second object 570 includes an RF coil that is not included in the at least one RF coil to be mounted on the first object 550. The apparatus 100 displays information about a third RF coil that is not to be mounted on the first object 550 but is to be mounted on the second object 570 and distinguishes the third RF coil information from the first and second RF coil information. The third RF coil is an RF coil to be additionally mounted on the apparatus 100 in order to image the second object 570 and is distinguished from the first and second RF coils that are pre-mounted to image the first object 550. The apparatus 100 displays a third RF abdomen RF coil model 710 corresponding to the third RF coil in a third color at a location corresponding to a mounting region of the third RF coil on the object model 612.

Since coil related characteristics, clinical purpose, channel number, and size of RF coils differ even when the RF coils are to be mounted on the same region, the apparatus 100 displays the third RF coil model 710 in the third color having brightness, chroma, shading, pattern and hue (or other visual attribute) changed in response to changed characteristics. A user readily identifies which RF coil is to be mounted based on a color of the third RF coil model 710 displayed on the display 500 of the apparatus 100.

Figure 8:
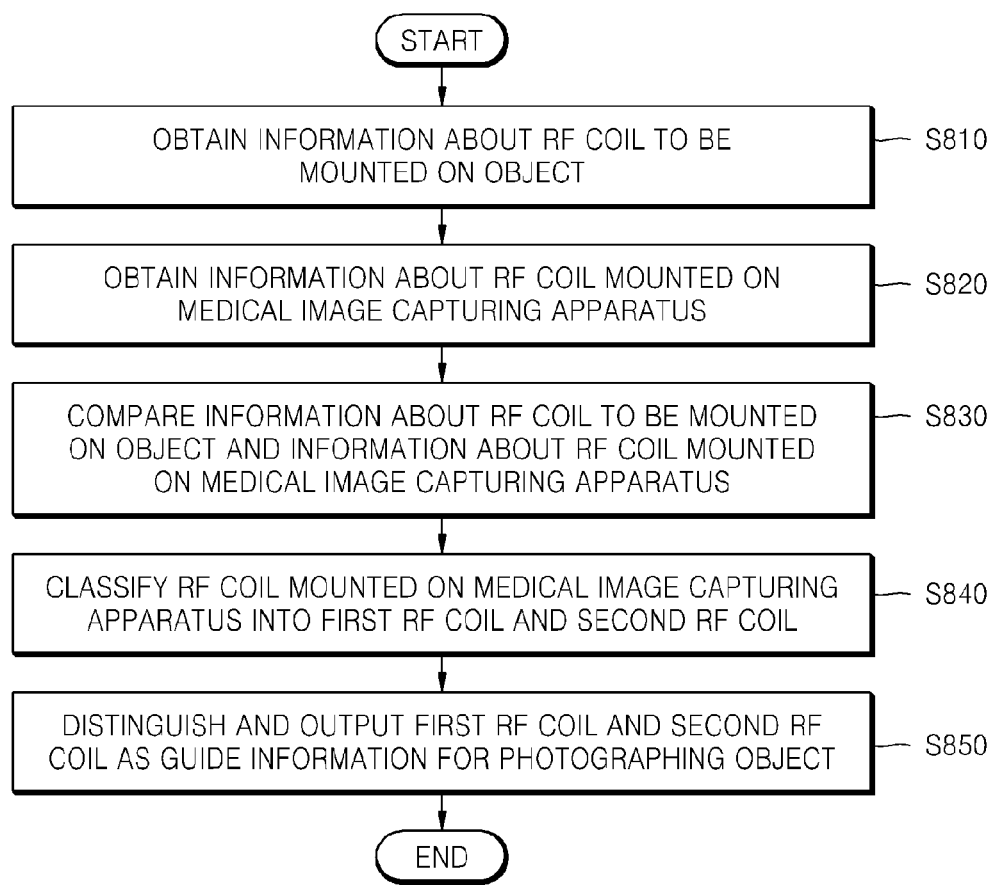
FIG. 8 shows a flowchart of a method of providing guide information, according to invention principles.

FIG. 8 shows a flowchart of a method of providing guide information. In operation 810, the apparatus 100 obtains information about at least one RF coil to be mounted next on an object. The information comprises, medical condition (e.g. disease) concerned, imaging mode, and imaged region of an object. In operation S820, the apparatus 100 obtains information about at least one RF coil currently mounted on the apparatus 100. The at least one RF coil is mounted on a gantry of the apparatus 100. The apparatus 100 determines a type of the at least one RF coil mounted on the apparatus 100 in response to received coil ID information. The at least one RF coil mounted on the apparatus 100 includes an RF coil mounted on the apparatus 100 for an object imaged before the object to be currently imaged. In operation S830, the apparatus 100 compares the information about the at least one RF coil to be mounted on the object and the information about the at least one RF coil currently mounted on the apparatus 100. In operation S840, the apparatus 100 classifies the at least one RF coil mounted on the apparatus 100 into a first RF coil to be mounted also on the object and a second RF coil not to be mounted on the object.

When head and leg RF coils are mounted on the apparatus 100, and the leg RF coil is to be mounted on the object, the apparatus 100 determines the leg RF coil as the first RF coil and the head RF coil as the second RF coil, for example. In operation S850, the apparatus 100 distinguishes and outputs the information about the first RF coil and the information about the second RF coil as guide information for imaging the object. A user determines which RF coil is to be removed from the apparatus 100 and which RF coil is not to be removed from the apparatus 100 based on the information about the first and second RF coils output from the apparatus 100. Also, the apparatus 100 outputs information about a third RF coil that is not mounted on the apparatus 100 but is to be mounted on the object and distinguishes the third RF coil information from the information about the first and second RF coils.

Apparatus 100 transmits ID information of the third RF coil to a plurality of RF coils that are not mounted on the apparatus 100. The apparatus 100 perform wireless communication with the plurality of RF coils that are not mounted on the apparatus 100, and transmits the ID information of the third RF coil to the plurality of RF coils by using wireless communication. Individual coils of the plurality of RF coils determine whether its own ID information corresponds to the ID information of the third RF coil. An RF coil corresponding to the ID information of the third RF coil from among the plurality of RF coils is identified to the user by outputting sound or light, message or another method. Accordingly, the user easily determines that the RF coil outputting sound or light is the third RF coil.

Figure 9A:
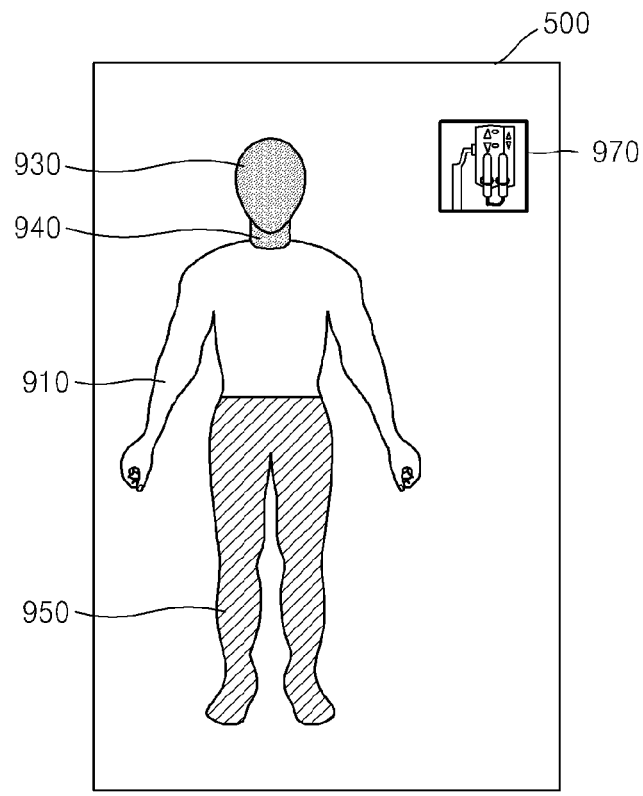
FIGS. 9A and 9B shows guide information output from the display of the medical image capturing apparatus, according to invention principles.
Figure 9B:
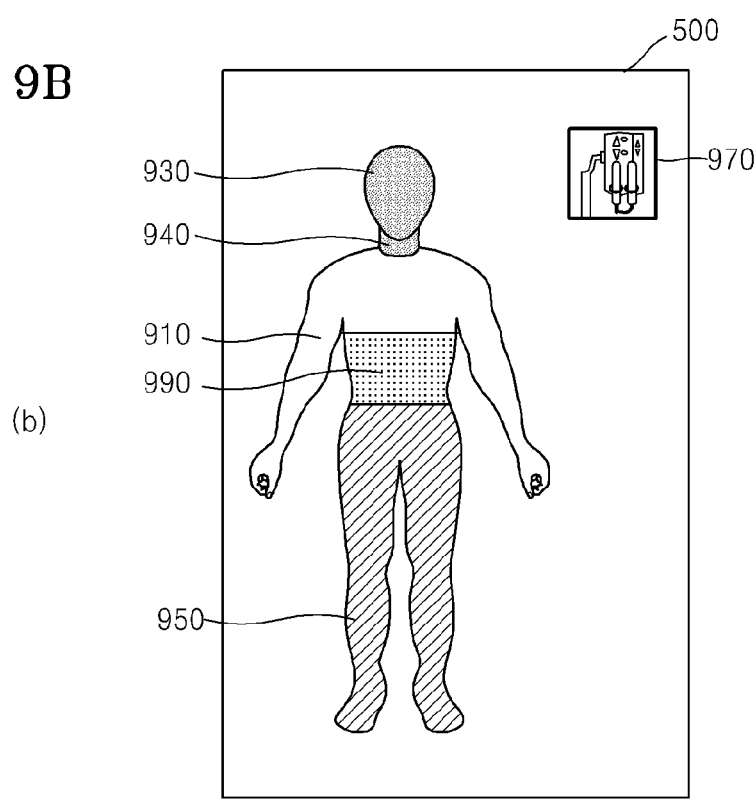

FIGS. 9A and 9B show guide information output from the display 500 of the apparatus 100. The apparatus 100 displays the guide information for imaging an object as the object model 910 and an RF coil model corresponding to the at least one RF coil mounted on the apparatus 100. The apparatus 100 displays the RF coil model at a location corresponding to a mounting region of the at least one RF coil mounted on the apparatus 100 on the object model 910. Alternatively, the apparatus 100 distinguishes the RF coil model into a first RF coil model corresponding to the first RF coil and a second RF coil model corresponding to the second RF coil, and displays the first and second RF coil models on the object model 910. For example, the apparatus 100 displays the first RF coil model in a first color and the second RF coil model in a second color. The user determines that the first RF coil model displayed in the first color is an RF coil to be kept on the apparatus 100, and the second RF coil model displayed on the second color is an RF coil to be removed from the apparatus 100.

Apparatus 100 displays a head RF coil model 930 and a neck RF coil model 940 in a first color indicating head and neck RF coils are to be retained for a next object to be imaged. Also, the apparatus 100 displays a leg RF coil model 950 in the second color indicating the leg RF coil is to be removed for a next object to be imaged. Also, the guide information of FIG. 9A includes a contrast medium injector model 970 as previously described.

Referring to FIG. 9B, the apparatus 100 displays a third RF coil model 990 corresponding to the third RF coil in a third color indicating the third coil it to be added for a next object to be imaged. The apparatus 100 outputs the guide information for imaging the object through the display 500 attached to the gantry of the apparatus 100. A user of a general medical image capturing apparatus recognizes imaging environment information of an object by using a display in an operating room, and changes an imaging environment in response to the guide information.

Figure 10A:
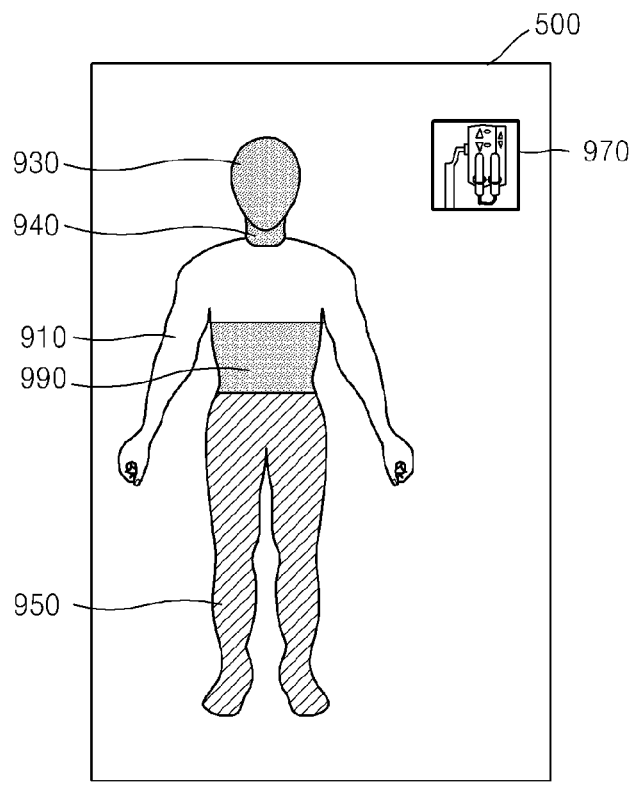
FIGS. 10A and 10B shows guide information output from the display of the medical image capturing apparatus, according to invention principles.
Figure 10B:
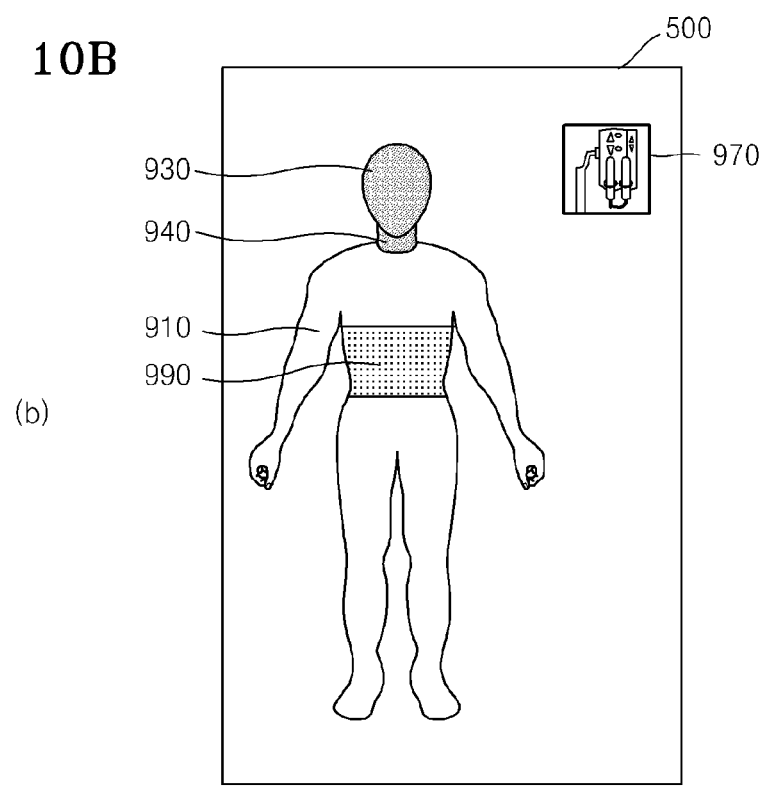

FIGS. 10A and 10B show guide information output from the display 500 of the apparatus 100. When the user removes an RF coil mounted on the apparatus 100 or additionally mounts an RF coil on the apparatus 100, the apparatus 100 outputs information about the RF coil removed from the apparatus 100 or the RF coil additionally mounted on the apparatus 100. Apparatus 100 outputs information about at least one RF coil mounted apparatus 100 in real-time. When the user mounts the third RF coil on the apparatus 100, the third RF coil model 990 displayed in the third color in FIG. 9B is changed to the first color, as shown in FIG. 10A. If the user mounts an RF coil that is not required for imaging the object on the apparatus 100, the apparatus 100 displays the RF coil mounted by the user in the second color so as to notify the user that a wrong RF coil has been mounted. Also, when an RF coil connected to the apparatus 100 is removed, the apparatus 100 deletes an RF coil model corresponding to the removed RF coil from the RF coil models displayed on the object model 910. When the user removes a leg RF coil from the apparatus 100, a leg RF coil model displayed on the guide information is deleted.

When the user of the general medical image capturing apparatus images a plurality of objects, the plurality of objects are imaged according to a predetermined stored order. However, when an imaging environment of a first object and an imaging environment of a second object that is imaged after the first object is very different, it takes a long time for the user to change an imaging environment which is substantially reduced using the system guide information. The apparatus 100 also recommends addition of resources e.g. RF coils in response to predetermined information associating resources e.g. RF coils with information including MR pulse sequences, patient medical record information and identification of an imaging system and version used.

Figure 11:
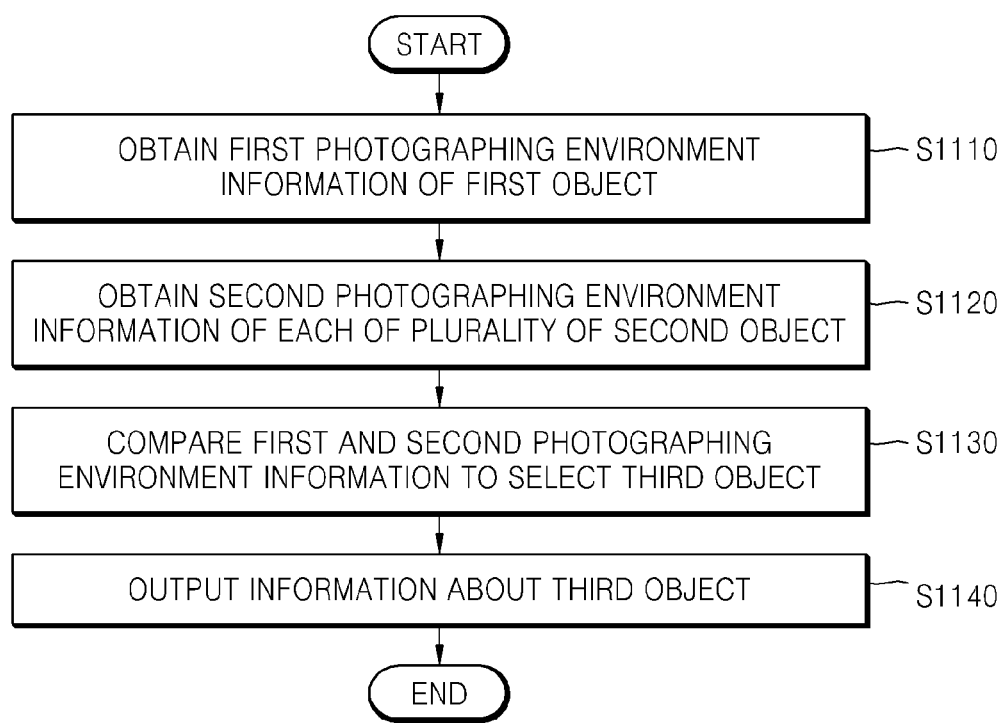
FIG. 11 shows a flowchart of a method of recommending an object, according to invention principles.

FIG. 11 shows a flowchart of a method of recommending an object. In operation S1110, the apparatus 100 obtains first imaging environment information of a first object. In operation S1120, the apparatus 100 obtains second imaging environment information of each of a plurality of second objects. The apparatus 100 obtains the first imaging environment information comprising information about a disease, an anatomical region to be imaged, and an imaging mode of the first object, and obtains the second imaging environment information comprising information about a patient medical condition (e.g., disease), an anatomical region to be imaged, and an imaging mode of each of the plurality of second objects. Alternatively, the apparatus 100 receives the first and second imaging environment information from an external server. The first and second imaging environment information includes information about at least one of a type of an RF coil mounted on an object, whether a contrast medium injector is used, whether an ECG measurer is used, whether a respiration measurer is used, and whether a temperature measurer is used.

In operation S1130, the apparatus 100 compares the first imaging environment information and the second imaging environment information to select a third object to be imaged after the first object from among the plurality of second objects. Different methods may be used to select the third object from the plurality of second objects. For example, the apparatus 100 determines an object that requires a minimum effort to change an imaging environment, based on types and the number of peripheral devices mounted with respect to the first object, and types and the number of peripheral devices mounted with respect to each of the plurality of second objects. In operation S1140, the apparatus 100 outputs information about the third object. The user determine the third object as an object to be imaged after the first object by referring to the information about the third object output by the apparatus 100.

FIGS. 12A and 12B show tables illustrating determining a third object from a plurality of second objects. FIG. 12A illustrates information about a first object. imaging environment information of "A" that is the first object indicates that a head RF coil and a leg RF coil are to be mounted on the apparatus 100 in order to image "A". FIG. 12B illustrates information about the plurality of second objects. From among the plurality of second objects, imaging environment information of "B" indicates that a neck RF coil is to be mounted to image "B", imaging environment information of "C" indicates that a head RF coil and a leg RF coil are to be mounted for "C", and imaging environment information of "D" indicates that a leg RF coil is to be mounted for "D".

The apparatus 100 identifies an object from a plurality of second objects having the same imaging configuration as a first object. Specifically, apparatus 100 identifies a third object (of the plurality of second objects) having the same type and number of RF coils as the first object. This enables a user to image the third object without having to change an imaging environment after imaging the first object. The apparatus 100 determines "C" as a third object having RF coils of the same type and number as "A". When there are two or more objects having RF coils of the same type and number as at least one RF coil to be mounted on the first object, the apparatus 100 determines the third object in response to whether a contrast medium injector is to be used. For example, when the imaging environment information of "A" indicates that a contrast medium injector is to be mounted for "A", the imaging environment information of "C" indicates that a contrast medium injector is not to be mounted for "C", and the imaging environment information of "D" indicates that a contrast medium injector is to be mounted for "D", the apparatus 100 determine "D" as the third object. An object of the second objects having the same type and number of RF coils as the first object, is determined as the third object.

FIGS. 13A and 13B show tables illustrating a method of determining a third object from among a second plurality of second objects. FIG. 13A illustrates information about the first object, and imaging environment information of "A" that is the first object indicates that a head RF coil and a leg RF coil are to be mounted for "A". FIG. 13B illustrates information about the plurality of second objects. From among the plurality of second objects, imaging environment information of "B" indicates that a neck RF coil is to be mounted for "B", imaging environment information of "C" indicates that a head RF coil, a leg RF coil, a neck RF coil, and an abdomen RF coil are to be mounted for "C", and imaging environment information of "D" indicates that a head RF coil, a leg RF coil, and an abdomen RF coil are to be mounted for "D".

If second object "B" imaging configuration does not match that of the first object, the apparatus 100 determines the closest configuration of "C" and "D" configurations in response to type and number of RF coils, for example. If an object requires many RF coils to be additionally mounted aside from at least one RF coil to be mounted on the first object, it take a lot of time to change an imaging environment. Apparatus 100 determines an object requiring least imaging system configuration change as having a least number of RF coils to be mounted in addition to those of the first object, as the third object. Apparatus 100 determines "D" as having the closest imaging configuration and least number of RF coils to be additionally mounted relative to "A", as the third object.

FIGS. 14A and 14B show tables illustrating a method of determining a third object from among a second plurality of second objects. When there are two or more objects on which the same number of RF coils are to be additionally mounted from among the second plurality of second objects as a first object, the apparatus 100 determines the third object based on a type of RF coils to be additionally mounted. For example, the user determines an RF coil order based on easiness of mounting an RF coil for an anatomical region, and determines the third object by considering mounting difficulty of an RF coil. Referring to FIG. 14B, imaging environment information of "C" indicates that a neck RF coil is used as well as head and neck RF coils of "A", and imaging environment information of "D" indicates that an abdomen RF coil is additionally mounted on "D" as well as head and leg RF coils. If it is determined by the user that the neck RF coil is easier to mount than the abdomen RF coil, the apparatus 100 determine "C" as the third object.

FIGS. 15A and 15B show tables illustrating a method of determining a third object from among a plurality of second objects. The apparatus 100 obtains information about the number and removal region of RF coils to be removed from those of a first object, with respect to each of the plurality of second objects, and selects the third object from among the plurality of second objects based on the number or removal regions. As shown in FIG. 15A, a head RF coil, an abdomen RF coil, a neck RF coil, and a leg RF coil are to be mounted on "A" the first object. Also, as shown in FIG. 15B, a neck RF coil is to be mounted on "B", a head RF coil and an abdomen RF coil are to be mounted on "C", and a head RF coil, an abdomen RF coil, and a leg RF coil are to be mounted on "D". The apparatus 100 determines "D" as having a least number of RF coils to be removed from RF coils mounted on "A", as the third object.

FIGS. 16A and 16B show tables illustrating a method of determining a third object from among a plurality of second objects. If there are two or more objects with the same number of RF coils to be removed the apparatus 100 hierarchically determines the third object based on a type of RF coils to be removed. Apparatus 100 determines a next object to be imaged in response to a hierarchical priority of differences in characteristics between a first object imaging configuration and imaging configurations needed for imaging a next object. For example, the user determines an RF coil order based on easiness of removal according to mounting regions, and determines the third object by considering the difficulty in removing of an RF coil to be removed from among the RF coils to be mounted on the first object.

Referring to FIG. 16B, a head RF coil, an abdomen RF coil, and a neck RF coil are to be mounted on "C", and a head RF coil, an abdomen RF coil, and a leg RF coil are to be mounted on "D". When "C" is imaged after "A", the user removes the leg RF coil mounted on "A", and when "D" is imaged after "A", the user removes the neck RF coil mounted on "A". When the user determines that it is easier to remove the neck RF coil than the leg RF coil, the apparatus 100 determines "D" as the third object from among "C" and "D". Alternatively, the apparatus 100 determines the similarity between RF coils to be mounted on the first object and RF coils to be mounted on each of the plurality of second objects, and determines an object having a highest similarity from among the plurality of second objects as the third object.

For example, the user determines similarity by adding a similarity value of 2 whenever RF coils for a second object include one RF coil mounted on a first object, subtract a similarity value of 2 whenever an RF coil not mounted on the first object is to be mounted on the second object, and subtracts a similarity value of 2 whenever an RF coil to be mounted on the first object includes an RF coil to be removed to image the second object. Here, a similarity value for determining the similarity varies according to types of RF coils and mounting regions.

Figure 17:
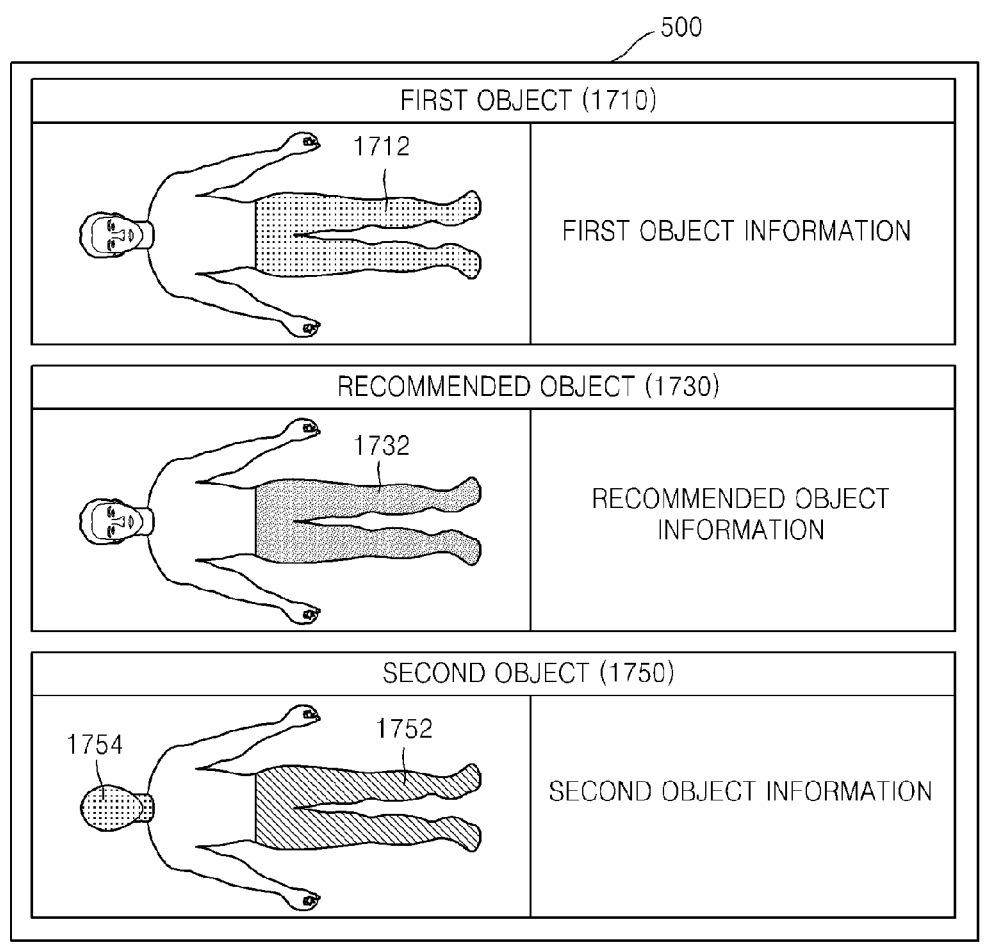
FIG. 17 shows guide information for photographing a first object, a second object, and a recommended object output by a display of the medical image capturing apparatus, according to invention principles.

FIG. 17 shows guide information for imaging a first object 1710, a second object 1750, and a recommended object 1730 output by the display 500 of the apparatus 100. The apparatus 100 outputs guide information for imaging the recommended object 1730 and recommending object 1730 as an object to be imaged after the first object 1710. Apparatus 100 classifies RF coils to be mounted on the first object 1710 into a first RF coil to be mounted on object 1730 and a second RF coil not to be mounted on object 1730, and outputs information about the first RF coil, information about the second RF coil, and information about a third RF coil that is not to be mounted on the first object 1710 but is to be mounted on the recommended object 1730.

Apparatus 100 displays a leg RF coil model 1712 corresponding to the leg RF coil to be mounted on the first object 1710, in a third color. When the leg RF coil is already mounted on the apparatus 100, the apparatus 100 display the leg RF coil model 1712 for the first object 1710 in a first color. Also, the apparatus 100 displays a leg RF coil model 1732 corresponding to the leg RF coil to be mounted on the recommended object 1730, in the first color so as to notify the user not to remove the leg RF coil to be mounted on the first object 1710 from the apparatus 100. Also, since the head RF coil to be mounted on the second object 1750 is not to be mounted on the first object 1710, the apparatus 100 display a head RF coil model 1754 corresponding to the head RF coil in the third color, and displays a leg RF coil model 1752 that is to be removed to image the second object 1750 in a second color.

Referring to FIG. 17, the apparatus 100 recommends, instead of the second object, the recommended object 1730 be imaged after imaging the first object 1710 since objects 1730 and 1710 use the same type and number of RF coils. When an imaging order is predetermined for a plurality of second objects, the apparatus 100 selects a third object from among second objects using predetermined rankings based on a first object. A predetermined imaging order of the plurality of second objects may be determined preventing objects being imaged out of order.

Figure 18:
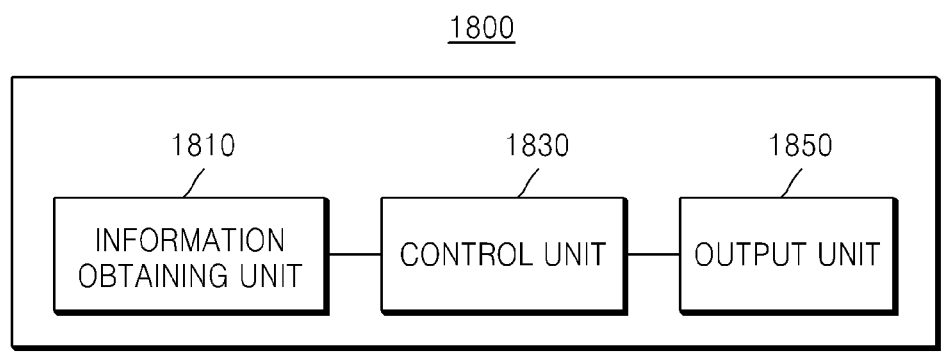
FIG. 18 shows a block diagram of a medical image capturing apparatus according to invention principles.

FIG. 18 is a block diagram of a medical image capturing apparatus 1800 including an information obtaining unit 1810, a control unit 1830, and an output unit 1850. The information obtaining unit 1810 and the control unit 1830 are configured as a microprocessor, for example. The information obtaining unit 1810 obtains the imaging environment information based on information about a medical condition (e.g., disease), an imaging mode, or an anatomical imaging region of the object, or receives the imaging environment information from an external server. The imaging environment information includes information about a type of an RF coil to be mounted on the object, whether a contrast medium injector is to be used for the object, whether an ECG measurer is to be used for the object, whether a respiration measurer is to be used for the object, and whether a temperature measurer is to be used for the object. Also, unit 1810 obtains information about RF coils to be mounted on the object, or RF coils mounted on the medical image capturing apparatus 1800.

The control unit 1830 compares first imaging environment information of a first object and second imaging environment information of a second object, and classifies the first imaging environment information into changing information and unchanging information for imaging the second object. Also, the control unit 1830 classifies at least one coil of the first object into a first RF coil to be mounted on both the first and the second objects and a second RF coil that is not to be mounted on the second object, or classifies at least one coil into a first RF coil to be mounted on an object and a second RF coil that is not to be mounted on the object. The control unit 1830 recommends a third object to be imaged after a first object. Control unit 1830 compares imaging environment information of the first object and imaging environment information of each of a plurality of second objects, and selects the third object to be imaged after imaging the first object from among the plurality of second objects. The output unit 1850 outputs guide information for imaging an object. The output unit 1850 includes a display that is attached to a gantry surface of the medical image capturing apparatus 1800. The output unit 1850 outputs information about a third object selected by the control unit 1830 from among a plurality of second objects. Also, although not illustrated in FIG. 18, the medical image capturing apparatus 1800 further includes a communication unit that transmits ID information of a third RF coil that is not mounted on the medical image capturing apparatus 1800 but is mounted on the object, to a plurality of RF coils that are not mounted on the medical image capturing apparatus 1800.

Figure 19:
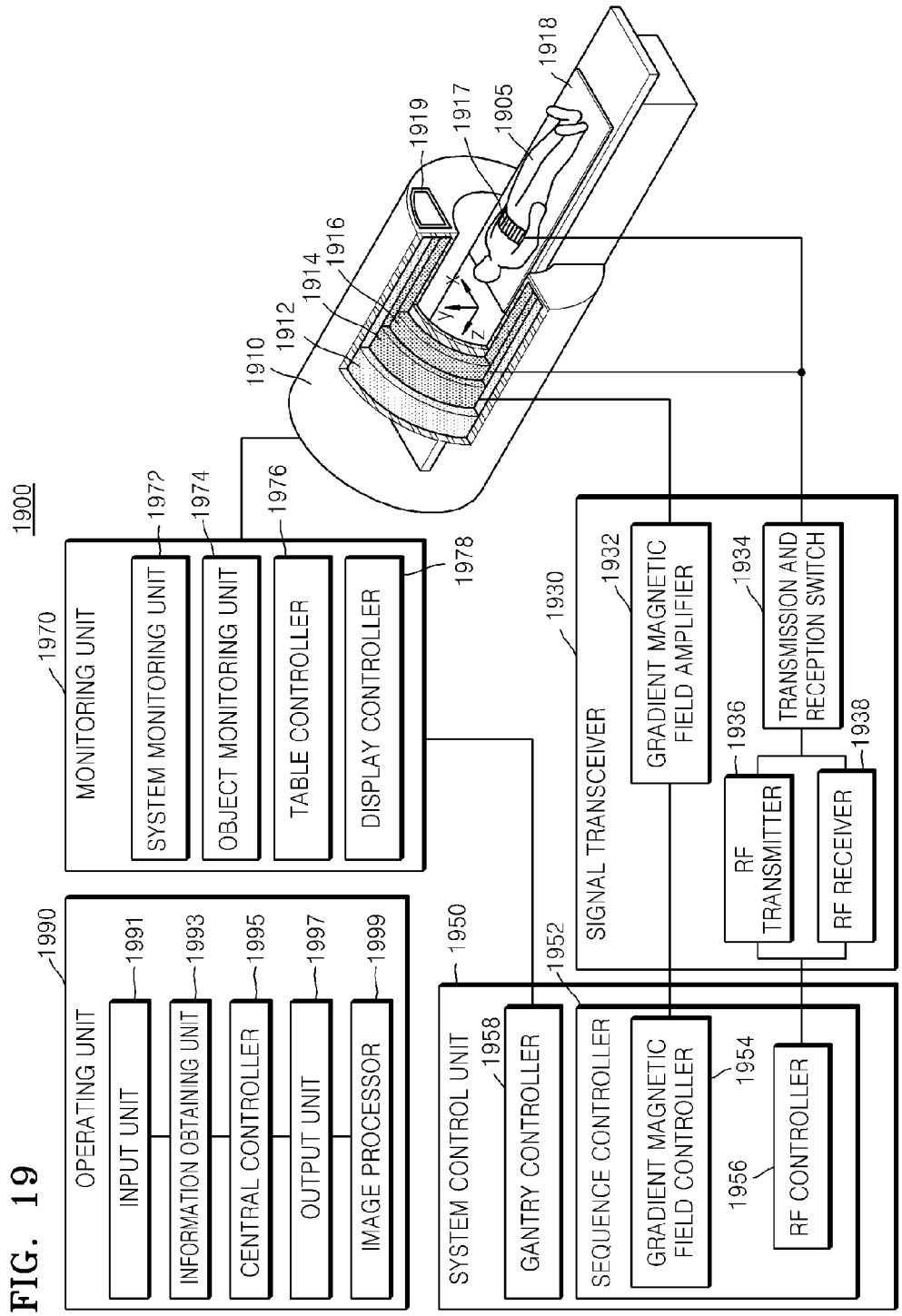
FIG. 19 shows a block diagram of a medical image capturing apparatus according to invention principles.

FIG. 19 shows a block diagram of an MRI medical image capturing apparatus 1900 including a gantry 1910, a signal transceiver 1930, a monitoring unit 1970, a system control unit 1950, and an operating unit 1990. The gantry 1910 blocks electromagnetic waves generated by a main magnet 1912, a gradient coil 1914, a fixed RF coil 1916, and a detachable RF coil 1917 from being externally emitted. A magnetostatic field and a gradient magnetic field are formed at a bore in the gantry 1910, and an RF signal is irradiated towards an object 1905. The main magnet 1912, the gradient coil 1914, and the fixed RF coil 1916 are arranged in a predetermined direction of the gantry 1910. The predetermined direction comprises along a coaxial cylinder direction. The object 1905 is disposed on a table 1918 that is inserted into a cylinder along a horizontal axis of the cylinder.

The main magnet 1912 generates a magnetostatic field or a static magnetic field for aligning a direction of magnetic dipole moments of atomic nuclei in the object 1905 in a constant direction. A precise and accurate MR image of the object 1905 is obtained when a magnetic field generated by the main magnet 1912 is strong and uniform.

The gradient coil 1914 includes X, Y, and Z coils for generating orthogonal gradient magnetic fields in X, Y, and Z-axis. The gradient coil 1914 provides location information of each region of the object 1905 by differently inducing resonance frequencies according to the regions of the object 1905. The fixed RF coil 1916 and the detachable RF coil 1917 irradiate an RF signal to a patient and receive an MR signal emitted from the object 1905. The fixed RF coil 1916 and the detachable RF coil 1917 transmit an RF signal at a same frequency as precessional motion towards atomic nuclei in precessional motion, stop transmitting the RF signal, and receive an MR signal emitted from the object 1905.

For example, in order to transit an atomic nucleus from a low energy state to a high energy state, the fixed RF coil 1916 and the detachable RF coil 1917 generate and apply an electromagnetic wave signal having an RF corresponding to a type of the atomic nucleus, for example, an RF signal, to the object 1905. When the electromagnetic wave signal generated by the fixed RF coil 1916 and the detachable RF coil 1917 is applied to the atomic nucleus, the atomic nucleus transit from the low energy state to the high energy state. Then, when electromagnetic waves generated by the fixed RF coil 1916 and the detachable RF coil 1917 disappear, the atomic nucleus on which the electromagnetic waves were applied transits from the high energy state to the low energy state, thereby emitting electromagnetic waves having a Lamor frequency. When applying the electromagnetic wave signal to the atomic nucleus is stopped, an energy level of the atomic nucleus is changed from a high energy level to a low energy level, and thus the atomic nucleus emit electromagnetic waves having a Lamor frequency. The fixed RF coil 1916 and the detachable RF coil 1917 receive electromagnetic wave signals from atomic nuclei in the object 1905.

The fixed RF coil 1916 and the detachable RF coil 1917 are realized as one RF transmitting and receiving coil having both a function of generating electromagnetic waves having a wireless frequency corresponding to a type of an atomic nucleus and a function of receiving electromagnetic waves emitted from an atomic nucleus. Alternatively, the fixed RF coil 1916 and the detachable RF coil 1917 are realized as a transmission RF coil having a function of generating electromagnetic waves having a wireless frequency corresponding to a type of an atomic nucleus, and a reception RF coil having a function of receiving electromagnetic waves emitted from an atomic nucleus.

The detachable RF coil 1917 comprises an RF coil for a part of the object, such as a head RF coil, a chest RF coil, a leg RF coil, a neck RF coil, a shoulder RF coil, a wrist RF coil, or an ankle RF coil. The detachable RF coil 1917 communicates with an external apparatus via wires and/or wirelessly, and also perform dual tune communication according to a communication frequency band. The detachable RF coil 1917 comprises a birdcage coil, a surface coil, or a transverse electromagnetic (TEM) coil. The detachable RF coil 1917 comprises a transmission exclusive coil, a reception exclusive coil, or a transmission and reception coil according to methods of transmitting and receiving an RF signal. The detachable RF coil 1917 comprises an RF coil in any one of various channels, such as 16 channels, 32 channels, 72 channels, and 144 channels.

The gantry 1910 further includes a display 1919 disposed outside the gantry 1910 and a display (not shown) disposed inside the gantry 1910. The gantry 1910 provides predetermined information to the user or the object through the displays. The signal transceiver 1930 controls the gradient magnetic field formed inside the gantry 1910, i.e., in the bore, according to a predetermined MR sequence, and control transmission and reception of an RF signal and an MR signal. The signal transceiver 1930 includes a gradient amplifier 1932, a transmission and reception switch 1934, an RF transmitter 1936, and an RF receiver 1938. The gradient amplifier 1932 drives the gradient coil 1914 in the gantry 1910, and supplies a pulse signal for generating a gradient magnetic field to the gradient coil 1914 according to control of a gradient magnetic field controller 1954. By controlling the pulse signal supplied from the gradient amplifier 1932 to the gradient coil 1914, gradient magnetic fields in X-, Y-, and Z-axis directions are derived.

The RF transmitter 1936 and the RF receiver 1938 drive the fixed RF coil 1916 and the detachable RF coil 1917. The RF transmitter 1936 supplies an RF pulse in a Lamor frequency to the fixed RF coil 1916 and the detachable RF coil 1917, and the RF receiver 1938 receives an MR signal received by the fixed RF coil 1916 and the detachable RF coil 1917. The transmission and reception switch 1934 adjusts transmitting and receiving directions of the RF signal and the MR signal. For example, the RF signal is irradiated to the object 1905 through the fixed RF coil 1916 and the detachable RF coil 1917 during a transmission mode, and the MR signal is received from the object 1905 through the fixed RF coil 1916 and the detachable RF coil 1917 during a reception mode. The transmission and reception switch 1934 is controlled by a control signal from an RF controller 1956.

The monitoring unit 1970 monitors or controls the gantry 1910 or devices mounted on the gantry 1910. The monitoring unit 1970 includes a system monitoring unit 1972, an object monitoring unit 1974, a table controller 1976, and a display controller 1978. The system monitoring unit 1972 monitors and controls a state of a magnetostatic field, a state of a gradient magnetic field, a state of an RF signal, a state of an RF coil, a state of a table, a state of a device measuring body information of an object, a power supply state, a state of a thermal exchanger, and a state of a compressor. The object monitoring unit 1974 monitors a state of the object 1905. Object monitoring unit 1974 includes a camera for observing movement or position of the object 1905, a respiration measurer for measuring the respiration of the object 1905, an ECG measurer for measuring ECG of the object 1905, or a temperature measurer for measuring a temperature of the object 1905, wherein the respiration measurer, the ECG measurer, or the temperature measurer are attached to and detached from the gantry 1910.

The table controller 1976 controls movement of the table 1918 where the object 1905 is positioned. The table controller 1976 controls the movement of the table 1918 according to sequence control of a sequence controller 1952. For example, during moving imaging of the object 1905, the table controller 1976 continuously or discontinuously moves the table 1918 according to the sequence control of the sequence controller 1952, and thus the object 1905 is imaged in a field of view (FOV) larger than that of the gantry 1910. The display controller 1978 controls the display 1919 and the display respectively outside and inside the gantry 1910. The display controller 1978 turns on or off the display 1919 and the display outside and inside the gantry 1910, and controls a screen to be output on the display 1919 and the display. Also, when a speaker is located inside or outside the gantry 1910, the display controller 1978 turns on or off the speaker or controls the speaker to output sound.

The system control unit 1950 includes the sequence controller 1952 for controlling a sequence of signals formed in the gantry 1910, and a gantry controller 1958 for controlling the gantry 1910 and devices mounted on the gantry 1910. The sequence controller 1952 includes the gradient magnetic field controller 1954 for controlling the gradient amplifier 1932, and the RF controller 1956 for controlling the RF transmitter 1936, the RF receiver 1938, and the transmission and reception switch 1934. The sequence controller 1952 controls the gradient amplifier 1932, the RF transmitter 1936, the RF receiver 1938, and the transmission and reception switch 1934 according to a pulse sequence received from the operating unit 1990. Here, the pulse sequence includes information required to control the gradient amplifier 1932, the RF transmitter 1936, the RF receiver 1938, and the transmission and reception switch 1934, for example, and includes information about strength, an application time, and an application timing of a pulse signal applied to the gradient coil 1914.

The operating unit 1990 requests the system control unit 1950 to transmit pulse sequence information while controlling an overall operation of the medical image capturing apparatus 1900. The operating unit 1990 includes an input unit 1991, an information obtaining unit 1993, a central controller 1995, an output unit 1997, and an image processor 1999. The user inputs object information, parameter information, a scan condition, a pulse sequence, or information about image composition or difference calculation by using the input unit 1991. The input unit 1991 includes a keyboard, a mouse, a track ball, a voice recognizer, a gesture recognizer, or a touch screen, or includes any one of other various input devices that are well known to one of ordinary skill in the art.

The information obtaining unit 1993 obtains imaging environment information of the object 1905. The information obtaining unit 1993 obtains the imaging environment information from an imaging order for performing the imaging examination and from a patient medical record and hospital information system. about the information indicates a medical condition (e.g., a disease), an imaging mode, and an anatomical region to be imaged of the object 1905, or receives the imaging environment information from an external server. The imaging environment information includes information about at least one of a type of an RF coil to be mounted on the object 1905, whether a contrast medium injector is to be used for the object 1905, whether an ECG measurer is to be used for the object 1905, whether a respiration measurer is to be used for the object 1905, and whether a temperature measurer is to be used for the object 1905. Also, the information obtaining unit 1993 obtains information about RF coils to be mounted on the object 1905, or information about RF coils mounted on the medical image capturing apparatus 1900. The central controller 1995 compares first imaging environment information of a first object and second imaging environment information of a second object, and classifies the first imaging environment information into changing information and unchanging information for imaging the second object. Also, the central controller 1995 classifies RF coils as previously described. The central controller 1995 recommends a third object to be imaged after a first object to the user. Central controller 1995 compares imaging environment information of the first object and imaging environment information of each of a plurality of second objects, and selects the third object to be imaged after the first object, from among the plurality of second objects.

The output unit 1997 outputs image data generated or rearranged by the image processor 1999 to the user. Also, the output unit 1997 outputs information required for the user to manipulate the medical image capturing apparatus 1900, such as user interface (UI), user information, or object information. The output unit 1997 includes a speaker, a printer, a cathode-ray tube (CRT) display, a liquid crystal display (LCD), a plasma display panel (PDP), an organic light-emitting device (OLED) display, a field emission display (FED), a light-emitting diode (LED) display, a vacuum fluorescent display (VFD), a digital light processing (DLP) display, a PFD display, a 3-dimensional (3D) display, or a transparent display, or any one of various output devices that are well known to one of ordinary skill in the art. The output unit 1997 outputs guide information for imaging the object 1905. The output unit 1997 includes display 1919 attached to a surface of the gantry 1910 of the medical image capturing apparatus 1900. The output unit 1997 outputs information about a third object selected by the central controller 1995 from among a plurality of second objects. The image processor 1999 processes an MR signal received from the RF receiver 1938 so as to generate MR image data of the object 1905.

The image processor 1999 performs various signal processes, such as amplification, frequency transformation, phase detection, low frequency amplification, and filtering, on an MR signal received by the RF receiver 1938. The image processor 1999 arranges digital data in a k space (for example, also referred to as a Fourier space or frequency space) of a memory, and rearranges the digital data into image data via 2D or 3D Fourier transformation. The image processor 1999 performs a composition process or difference calculation process on image data if required. The composition process includes an addition process on a pixel or a maximum intensity projection (MIP) process. The image processor 1999 stores not only rearranged image data but also image data on which a composition process or difference calculation process is performed, in a memory (not shown) or an external server.

Signal processes applied to MR signals by the image processor 1999 are performed in parallel. For example, signal processing is performed on a plurality of MR signals received by a multi-channel RF coil in parallel so as to rearrange the plurality of MR signals as image data. The signal transceiver 1930, the monitoring unit 1970, the system control unit 1950, and the operating unit 1990 are separate components in FIG. 19, but it is obvious to one of ordinary skill in the art that functions of the signal transceiver 1930, the monitoring unit 1970, the system control unit 1950, and the operating unit 1990 may be performed by one or more components. For example, the image processor 1999 converts an MR signal received by the RF receiver 1938 into a digital signal, but such a conversion to a digital signal may be instead directly performed by the RF receiver 1938, the fixed RF coil 1916, or the detachable RF coil 1917.

The gantry 1910, the fixed RF coil 1916, the detachable RF coil 1917, the signal transceiver 1930, the monitoring unit 1970, the system control unit 1950, and the operating unit 1990 are connected to each other via wires or wirelessly, and when they are connected wirelessly, the medical image capturing apparatus 1900 further includes an apparatus (not shown) for synchronizing clocks therebetween. Communication between the gantry 1910, the fixed RF coil 1916, the detachable RF coil 1917, the signal transceiver 1930, the monitoring unit 1970, the system control unit 1950, and the operating unit 1990 is performed by using a high-speed digital interface, such as low voltage differential signaling (LVDS), asynchronous serial communication, such as universal asynchronous receiver transmitter (UART), a low-delay network protocol, such as an asynchronous serial communication or controller area network (CAN), or optical communication, or any other communication method that is well known to one of ordinary skill in the art.

Figure 20:
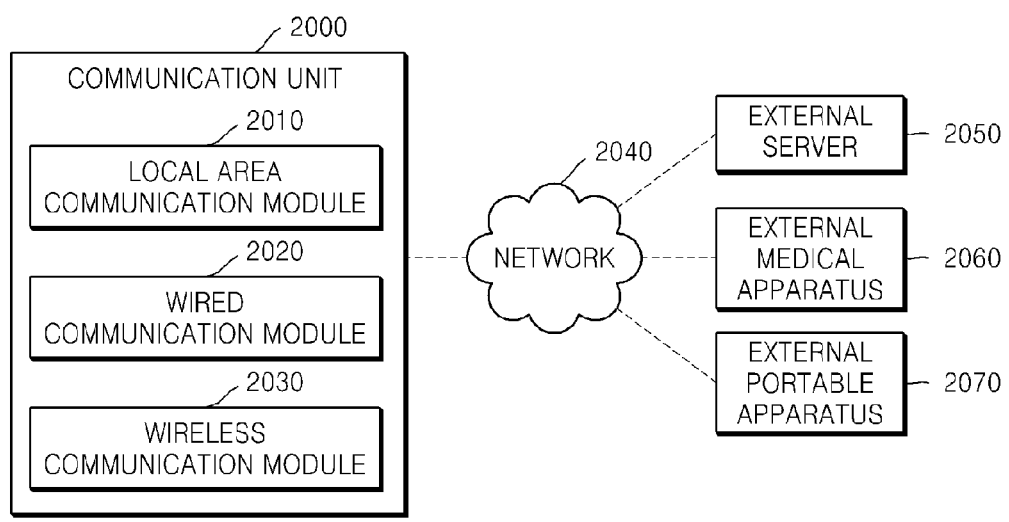
FIG. 20 shows a block diagram of a communication unit included in the medical image capturing apparatus of FIG. 19, according to invention principles.

FIG. 20 shows a communication unit 2000 included in the medical image capturing apparatus 1900 of FIG. 19. The communication unit 2000 is connected to at least one of the gantry 1910, the signal transceiver 1930, the monitoring unit 1970, the system control unit 1950, and the operating unit 1990 of FIG. 19. The communication unit 2000 transmits and receives data to and from a hospital server or another medical apparatus in a hospital connected through a picture archiving and communication system (PACS), and performs data communication according to the digital imaging and communications in medicine (DICOM) standard. The communication unit 2000 is connected to a network 2040 via wires or wirelessly to communicate with an external server 2050, an external medical apparatus 2060, or an external portable apparatus 2070.

The communication unit 2000 transmits and receives data related to the diagnosis of an object through the network 2040, and also transmits and receives a medical image captured by the external medical apparatus 2060, such as a CT, an MRI, or an X-ray apparatus. In addition, the communication unit 2000 receives a diagnosis history or a treatment schedule of the object from the external server 2050 to diagnose the object. The communication unit 2000 performs data communication not only with the external server 2050 or external medical apparatus 2060 in a hospital, but also with the external portable apparatus 2070, such as a mobile phone, a personal digital assistant (PDA), or a laptop of a doctor or customer. Also, the communication unit 2000 transmits information about malfunction of the medical image capturing apparatus 1900 or about medical image quality to a user through the network 2040, and receives feedback from the user.

The communication unit 2000 includes at least one component enabling communication with an external apparatus, for example, a local area communication module 2010, a wired communication module 2020, and a wireless communication module 2030. The local area communication module 2010 is a module for performing local area communication with a device within a predetermined distance. Examples of a local area communication technology include a wireless local area network (LAN), Wi-Fi, Bluetooth, Zigbee, Wi-Fi direct (WFD), ultra wideband (UWB), infrared data association (IrDA), Bluetooth low energy (BLE), and near field communication (NFC), for example. The wired communication module 2020 is a module for performing communication by using an electric signal or an optical signal. Examples of a wired communication technology include wired communication technologies using a pair cable, a coaxial cable, and an optical fiber cable, and other well known wired communication technologies. The wireless communication module 2030 transmits and receives a wireless signal to and from at least one of a base station, an external apparatus, and a server in a mobile communication network. Here, the wireless signal include data in any one of various formats according to transmitting and receiving a voice call signal, a video call signal, and a text/multimedia message. The system embodiments may comprise programs executable by a computer and can be implemented in general-use digital computers that execute the programs using a computer-readable recording medium. Examples of the computer-readable recording medium include magnetic storage media (e.g., ROM, floppy disks, hard disks, etc.), optical recording media (e.g., CD-ROMs or DVDs), etc.

While the present invention has been particularly shown and described with reference to exemplary embodiments thereof, it will be understood by those of ordinary skill in the art that various changes in form and details are made therein without departing from the spirit and scope of the present invention as defined by the following claims.

The above-described embodiments can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. The functions and process steps herein may be performed automatically or wholly or partially in response to user command. An activity (including a step) performed automatically is performed in response to executable instruction or device operation without user direct initiation of the activity. No claim element herein is to be construed under the provisions of 35 U.S.C. 112, sixth paragraph, unless the element is expressly recited using the phrase "means for."

What is claimed is:

1. A method of providing guidance information for guiding acquisition of medical images of an object using a medical imaging system, the method comprising:
    obtaining first imaging configuration information of a first object and second imaging configuration information of a second object;
    classifying the first imaging configuration information into changing information indicating a difference between the first and second imaging configuration and unchanging information indicating no difference between the first and second imaging configuration, by comparing the first imaging configuration information and the second imaging configuration information;
    displaying the changing information as guide information for imaging the second object;
    determining an imaging configuration of the medical imaging system based on the changing information and the unchanging information; and
    acquiring a medical image of the second object using the medical imaging system based on the determined imaging configuration,
    wherein the displaying comprises displaying information identifying how the changing information is to be changed to image the second object.

2. The method of claim 1, wherein the imaging configuration information comprises:
    information identifying a type of at least one radio frequency (RF) coil to be mounted on an object; and
    information identifying at least one of:
    whether a contrast medium injector is to be used for an object;
    whether an electrocardiogram (ECG) device is to be used for an object;
    whether a respiration device is to be used for an object; and
    whether a temperature measurement device is to be used for an object.

3. The method of claim 2, wherein the classifying comprises classifying the at least one RF coil to be mounted on the first object into a first RF coil to be mounted also on the second object or a second RF coil not to be mounted on the second object, and the displaying comprises distinguishing and displaying information identifying the first RF coil and information identifying the second RF coil.

4. The method of claim 3, wherein the classifying comprises classifying the at least one RF coil into the first RF coil and the second RF coil in response to at least one of, mounting anatomical region, channel number, clinical purpose, and size of RF coil.

5. The method of claim 3, wherein the displaying comprises displaying information identifying a third RF coil that is not to be mounted on the first object but to be mounted on the second object by distinguishing the information identifying the third RF coil from the information identifying the first and second RF coils.

6. The method of claim 3, wherein the displaying comprises displaying an RF coil model corresponding to the at least one RF coil to be mounted on the first object at a location of an object model displayed on the display, the location corresponding to a mounting region of the at least one RF coil to be mounted on the first object.

7. The method of claim 6, wherein the displaying comprises displaying a first RF coil model in a first color, and displaying a second RF coil model in a second color.

8. The method of claim 7, wherein the displaying comprises displaying a third RF coil model corresponding to a third RF coil that is not to be mounted on the first object but to be mounted on the second object in a third color at a location corresponding to a mounting region of the third RF coil on the object model.

9. The method of claim 8, wherein the displaying the third RF coil model in the third color comprises displaying the third RF coil model in the third color, wherein at least one of brightness, chroma, and hue of the third color is changed in response to at least one of an anatomical mounting region, a clinical purpose, a channel number, and a size of the third RF coil.

10. A non-transitory computer-readable recording medium having recorded thereon a program for executing the method of claim 1.

11. A method of providing guidance information for guiding sequencing and acquisition of medical images of an object using a medical imaging system, the method comprising:
    obtaining information identifying at least one radio frequency (RF) coil to be mounted on an object and information identifying at least one RF coil mounted on a medical image acquisition apparatus;
    classifying the at least one RF coil mounted on the medical image acquisition apparatus into a first RF coil to be mounted also on the object or a second RF coil that is not to be mounted on the object, by comparing the information identifying the at least one RF coil to be mounted on the object and the information identifying the at least one RF coil mounted on the medical image acquisition apparatus;
    displaying guidance information identifying the first RF coil and information identifying the second RF coil and distinguishing the first and second RF coils for use in imaging the object,
    determining an imaging configuration of the medical imaging system with respect to the at least one RF coil based on the guidance information; and
    acquiring a medical image of the object using the medical imaging system based on the determined imaging configuration of the medical imaging system.

12. The method of claim 11, wherein the displaying comprises displaying information identifying a third RF coil that is not mounted on the medical image acquisition apparatus but is to be mounted on the object, by distinguishing the information identifying the third RF coil from the information identifying the first and second RF coils.

13. The method of claim 12, further comprising transmitting identification information of the third RF coil to a plurality of RF coils that are not mounted on the medical image acquisition apparatus.

14. The method of claim 11, wherein the displaying comprises displaying the information identifying the first RF coil and the information identifying the second RF coil on a display.

15. The method of claim 14, wherein the displaying comprises displaying the information identifying the first RF coil and the information identifying the second RF coil on a display attached to a gantry surface of the medical image acquisition apparatus.

16. The method of claim 14, wherein the displaying comprises displaying an RF coil model corresponding to the at least one RF coil mounted on the medical image acquisition apparatus at a location corresponding to a mounting region of the at least one RF coil mounted on the medical image acquisition apparatus, from among an object model displayed on the display.

17. The method of claim 16, wherein the displaying comprises displaying a first RF coil model corresponding to the first RF coil in a first color and a second RF coil model corresponding to the second RF coil in a second color, on an RF coil model displayed on the object model.

18. The method of claim 17, wherein the displaying comprises displaying a third RF coil model corresponding to a third RF coil that is not mounted on the medical image acquisition apparatus but is to be mounted on the object, in a third color at a location corresponding to a mounting region of the third RF coil on the object model.

19. The method of claim 18, wherein the displaying comprises, when the third RF coil is mounted on the medical image acquisition apparatus, displaying the third RF coil model displayed on the object model in the first color changed from the third color.

20. The method of claim 16, wherein the displaying comprises, when an RF coil mounted on the medical image acquisition apparatus is removed, not displaying of an RF coil model corresponding to the RF coil removed from the medical image acquisition apparatus on the object model.

21. A method of selecting an object to be imaged using a medical imaging system, the method comprising:
    obtaining first imaging configuration information identifying a first object;
    obtaining second imaging configuration information identifying each of a plurality of second objects;
    selecting a third object to be imaged after the first object is imaged, from among the plurality of second objects, by comparing the first imaging configuration information and the second imaging configuration information identifying each of the plurality of second objects;
    displaying information identifying the selected third object,
    determining an imaging configuration of the medical imaging system based on imaging configuration information identifying the third object from among the second imaging configuration information; and
    acquiring a medical image of the third object using the medical imaging system based on the determined imaging configuration of the medical imaging system,
    wherein the imaging configuration information comprises information identifying a type of at least one radio frequency (RF) coil to be mounted on an object.

22. The method of claim 21, wherein the imaging configuration information further comprises information identifying at least one of,
    whether a contrast medium injector is to be used for an object,
    whether an electrocardiogram (ECG) device is to be used for an object, whether a respiration device is to be used for an object, and whether a temperature measurement device is to be used for an object.

23. The method of claim 21, wherein the selecting of the third object comprises selecting an object to be imaged using the same number and type of RF coils as used in imaging the first object.

24. The method of claim 21, wherein the selecting of the third object comprises:
   determining a second plurality of second objects on which at least one RF coil used in imaging the first object is to be mounted and at least one RF coil that is not used in imaging the first object is to be additionally mounted; and
   selecting the third object from among the determined second plurality of second objects based on the number of RF coils to be additionally mounted on the second plurality of second objects.

25. The method of claim 24, wherein the selecting of the third object from among the determined second plurality of second objects comprises selecting an object on which the least number RF coils are to be additionally mounted.

26. The method of claim 21, wherein the selecting of the third object comprises:
   obtaining information identifying a number of RF coils to be removed from the at least one RF coil to be mounted on the first object for imaging each of the plurality of second objects; and
   selecting the third object from among the plurality of second objects based on the obtained information identifying the number of RF coils.

27. The method of claim 26, wherein the selecting of the third object from among the plurality of second objects comprises selecting an object having the least number of RF coils to be removed as the third object, from among the plurality of second objects.

28. The method of claim 21, wherein the selecting of the third object comprises:
   determining the similarity between the at least one RF coil to be mounted on the first object and at least one RF coil to be mounted on each of the plurality of second objects; and
   selecting a second object having the highest similarity from among the plurality of second objects, as the third object.

29. The method of claim 28, wherein the determining of the similarity comprises:
   setting a similarity value according to mounting regions of each RF coil; and
   determining the similarity between the at least one RF coil to be mounted on the first object and the at least one RF coil to be mounted on each of the plurality of second objects based on the set similarity value.

30. The method of claim 21, wherein the selecting of the third object comprises, when an imaging order of the plurality of second objects is predetermined, selecting the third object from second objects in response to the predetermined order.

31. The method of claim 21, wherein the displaying comprises displaying changing information for imaging the third object from among the first imaging configuration information, as guide information for imaging the third object.

32. A non-transitory computer-readable recording medium having recorded thereon a program for executing the method of claim 21.

33. A medical image acquisition apparatus comprising:
   at least one processor configured to obtain first imaging configuration information of a first object and second imaging configuration information of a second object and classify the first imaging configuration information into:
      changing information indicating a difference between the first and second imaging configuration and
      unchanging information indicating no difference between the first and second imaging configuration, by comparing the first imaging configuration information and the second imaging configuration information; and
   a display for displaying the changing information as guide information for imaging the second object,
   wherein the at least one processor is further configured to:
      determine an imaging configuration of the medical image acquisition apparatus based on the changing information and the unchanging information; and
   acquire a medical image of the second object based on the determined imaging configuration, and
   wherein the display displays information identifying how the changing information is to be changed to image the second object.

34. The medical image acquisition apparatus of claim 33, wherein the at least one processor identifies, based on the imaging configuration information:
   a type of at least one radio frequency (RF) coil to be mounted on an object; and
   at least one of:
   whether a contrast medium injector is to be used for an object;
   whether an electrocardiogram (ECG) device is to be used for an object;
   whether a respiration device is to be used for an object; and
   whether a temperature measurement device is to be used for an object.

35. The medical image acquisition apparatus of claim 34, wherein the at least one processor classifies the at least one RF coil to be mounted on the first object into a first RF coil to be mounted also on the second object or a second RF coil not to be mounted on the second object, and
   the display displays information identifying the first RF coil and information identifying the second RF coil.

36. The medical image acquisition apparatus of claim 35, wherein the at least one processor classifies the at least one RF coil to be mounted on the first object into the first RF coil and the second RF coil based on at least one of, mounting anatomical region, channel number, clinical purpose, and size of an RF coil to be mounted on the first object.

37. The medical image acquisition apparatus of claim 35, wherein the display displays information identifying a third RF coil that is not to be mounted on the first object but to be mounted on the second object by distinguishing the information identifying the third RF coil from the information identifying the first and second RF coils.

38. The medical image acquisition apparatus of claim 35, wherein the display displays an RF coil model on an object model displayed on the display, at a location on the object model corresponding to a mounting region of the first object on which the first RF coil is mounted or a location on the object model corresponding to a mounting region of the first object on which the second RF coil is mounted.

39. The medical image acquisition apparatus of claim 38, wherein the display displays a first RF coil model in a first color on the object model, at the location on the object model corresponding to the mounting region of the first object on which the first RF coil is mounted, and displays a second RF coil model in a second color on the object model, at the location on the object model corresponding to the mounting region of the first object on which the second RF coil is mounted, wherein the first RF coil model and the second RF coil model are included in the RF coil model.

40. The medical image acquisition apparatus of claim 39, wherein the display displays a third RF coil model in a third color on the object model, at a location on the object model corresponding to a mounting region of the second object on which a third RF coil is to be mounted, wherein the third RF coil is not to be mounted on the first object.

41. The medical image acquisition apparatus of claim 40, wherein the display changes at least one of brightness, chroma, and hue of the third color according to at least one of an anatomical mounting region, a clinical purpose, a channel number, and a size of the third RF coil.

42. A medical image acquisition apparatus on which at least one radio frequency (RF) coil is mounted, the apparatus comprising:

at least one processor configured to obtain information identifying at least one RF coil to be mounted on an object and information identifying at least one RF coil mounted on the medical image acquisition apparatus, and classify the at least one RF coil mounted on the medical image acquisition apparatus as a first RF coil also to be mounted on the object or a second RF coil not to be mounted on the object, by comparing the information identifying the at least one RF coil to be mounted on the object and the information identifying the at least one RF coil mounted on the medical image acquisition apparatus; and a display for displaying guidance information identifying the first RF coil and information identifying the second RF coil and distinguishing the first and second RF coils for imaging the object, wherein the at least one processor is further configured to:
 determine an imaging configuration of the medical image acquisition apparatus with respect to the at least one RF coil based on the guidance information; and
 acquire a medical image of the object based on the determined imaging configuration of the medical image acquisition apparatus.

43. The medical image acquisition apparatus of claim 42, wherein the display displays information identifying a third RF coil that is not mounted on the medical image acquisition apparatus but is to be mounted on the object, by distinguishing the information identifying the third RF coil from the information identifying the first and second RF coils.

44. The medical image acquisition apparatus of claim 43, wherein the at least one processor is further configured to transmit identification information of the third RF coil to a plurality of RF coils that are not mounted on the medical image acquisition apparatus.

45. The medical image acquisition apparatus of claim 42, wherein the display is attached to a gantry surface of the medical image acquisition apparatus.

46. The medical image acquisition apparatus of claim 42, wherein the display displays an RF coil model on an object model displayed on the display, at a location corresponding to a mounting region of a first object on which the first RF coil is mounted or a location corresponding to a mounting region of the first object on which the second RF coil is mounted.

47. The medical image acquisition apparatus of claim 46, wherein the display displays a first RF coil model in a first color on the object model, at the location on the object model corresponding to the mounting region of the first object on which the first RF coil is mounted, and displays a second RF coil model in a second color on the object model, at the location on the object model corresponding to the mounting region of the first object on which the second RF coil is mounted, wherein the first RF coil model and the second RF coil model are included in the RF coil model.

48. The medical image acquisition apparatus of claim 47, wherein the display displays a third RF coil model in a third color on the object model, at a location on the object model corresponding to a mounting region of the second object on which a third RF coil is to be mounted, wherein the third RF coil is not mounted on the medical image acquisition apparatus.

49. The medical image acquisition apparatus of claim 47, wherein wherein the display displays a third RF coil model in a third color on the object model, and when the third RF coil is mounted on the medical image acquisition apparatus, the display changes the third RF coil model to the first color.

50. The medical image acquisition apparatus of claim 47, wherein the display, respectively removes the first RF coil model or the second RF coil model from the object model when the first RF coil or the second RF coil is removed from the medical image acquisition apparatus.

51. A medical image acquisition apparatus for recommending an object, the medical image acquisition apparatus comprising:

at least one processor obtain first imaging configuration information identifying a first object, and second imaging configuration information identifying each of a plurality of second objects, and select a third object to be imaged after the first object is imaged, from among the plurality of second objects, by comparing the first imaging configuration information and the second imaging configuration information identifying each of the plurality of second objects; and a display for displaying information identifying the selected third object, wherein the at least one processor is further configured to:
 determine an imaging configuration of the medical image acquisition apparatus based on imaging configuration information identifying the third object from among the second imaging configuration information; and
 acquire a medical image of the third object based on the determined imaging configuration of the medical image acquisition apparatus, wherein the imaging configuration information comprises information identifying a type of at least one radio frequency (RF) coil to be mounted on an object.

52. The medical image acquisition apparatus of claim 51, wherein the at least one processor identifies, based on the imaging configuration information, at least one of:

whether a contrast medium injector is to be used for an object;

whether an electrocardiogram (ECG) device is to be used for an object;

whether a respiration device is to be used for an object; and whether a temperature measurement device is to be used for an object.

53. The medical image acquisition apparatus of claim 51, wherein the at least one processor selects an object on which at least one RF coil that is in a same type and in the same number as the at least one RF coil to be mounted on the first object is to be mounted, from among the plurality of second objects, as the third object.

54. The medical image acquisition apparatus of claim 51, wherein the at least one processor determines a second plurality of second objects on which the at least one RF coil to be mounted on the first object is to be mounted and at least one RF coil that is not to be mounted on the first object is to be additionally mounted, and selects the third object from among the determined second plurality of second objects based on the number of the at least one RF coil to be additionally mounted on the second plurality of second objects.

55. The medical image acquisition apparatus of claim 54, wherein the at least one processor selects an object on which the least number of the at least one RF coil are to be additionally mounted from among the determined second plurality of second objects, as the third object.

56. The medical image acquisition apparatus of claim 51, wherein the at least one processor obtains information about a number of RF coils to be removed from the at least one RF coil to be mounted on a first object for imaging each of the plurality of second objects, and selects the third object from among the plurality of second objects based on the obtained information about the number of the at least one RF coil to be removed.

57. The medical image acquisition apparatus of claim 56, wherein the at least one processor selects an object having the least number of the at least one RF coil to be removed as the third object, from among the plurality of second objects.

58. The medical image acquisition apparatus of claim 51, wherein the at least one processor determines the similarity between the at least one RF coil to be mounted on the first object and at least one RF coil to be mounted on each of the plurality of second objects, and selects a second object having the highest similarity from among the plurality of second objects, as the third object.

59. The medical image acquisition apparatus of claim 58, wherein the at least one processor sets a similarity value according to mounting regions of each RF coil, and determines the similarity between the at least one RF coil to be mounted on the first object and the at least one RF coil to be mounted on each of the plurality of second objects based on the set similarity value.

60. The medical image acquisition apparatus of claim 51, wherein the at least one processor, when an imaging order of the plurality of second objects is predetermined, selects the third object from second objects within predetermined rankings.

61. The medical image acquisition apparatus of claim 51, wherein the display displays changing information for imaging the third object from among the first imaging configuration information, as guide information for imaging the third object.

* * * * *